United States Patent
Suciu-Foca et al.

(10) Patent No.: US 10,765,742 B2
(45) Date of Patent: Sep. 8, 2020

(54) METHODS OF TREATING CD166-EXPRESSING CANCER

(71) Applicants: Nicole Suciu-Foca, New York, NY (US); George Vlad, Forest Hills, NY (US); Zheng Xu, New York, NY (US)

(72) Inventors: Nicole Suciu-Foca, New York, NY (US); George Vlad, Forest Hills, NY (US); Zheng Xu, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 15/745,582

(22) PCT Filed: Jul. 18, 2016

(86) PCT No.: PCT/US2016/042833
§ 371 (c)(1),
(2) Date: Jan. 17, 2018

(87) PCT Pub. No.: WO2017/015227
PCT Pub. Date: Jan. 26, 2017

(65) Prior Publication Data
US 2018/0207269 A1    Jul. 26, 2018

Related U.S. Application Data

(60) Provisional application No. 62/193,980, filed on Jul. 17, 2015.

(51) Int. Cl.
| | | |
|---|---|---|
| A61K 39/00 | (2006.01) | |
| A61K 39/395 | (2006.01) | |
| C07K 16/28 | (2006.01) | |
| G01N 33/574 | (2006.01) | |
| A61K 38/17 | (2006.01) | |
| A61P 35/00 | (2006.01) | |

(52) U.S. Cl.
CPC .... *A61K 39/39558* (2013.01); *A61K 38/1774* (2013.01); *A61P 35/00* (2018.01); *C07K 16/2803* (2013.01); *G01N 33/574* (2013.01); *G01N 33/57492* (2013.01); *C07K 2317/76* (2013.01); *G01N 2800/52* (2013.01)

(58) Field of Classification Search
CPC .............................. A61K 39/00; A61K 38/177
See application file for complete search history.

(56) References Cited

U.S. PATENT DOCUMENTS

| | | | |
|---|---|---|---|
| 4,515,895 A | 5/1985 | Kung et al. | |
| 4,652,447 A | 3/1987 | Kung et al. | |
| 4,658,020 A | 4/1987 | Kung et al. | |
| 4,677,056 A | 6/1987 | Dupont et al. | |
| 4,816,404 A | 3/1989 | Suciu-Foca et al. | |
| 4,818,689 A | 4/1989 | Suciu-Foca et al. | |
| 5,156,951 A | 10/1992 | Bach et al. | |
| 6,384,203 B1 | 5/2002 | Anderson et al. | |
| 6,667,175 B1 | 12/2003 | Suciu-Foca | |
| 6,759,239 B2 | 7/2004 | Suciu-Foca et al. | |
| 7,144,728 B1 | 12/2006 | Suciu-Foca et al. | |
| 7,777,008 B2 | 8/2010 | Ponath et al. | |
| 7,834,157 B2 | 11/2010 | Cosman | |
| 8,003,762 B2 | 8/2011 | Tsukamoto et al. | |
| 8,142,994 B2 | 3/2012 | Moorhouse et al. | |
| 8,207,110 B2 | 6/2012 | Suciu-Foca et al. | |
| 8,299,016 B2 | 10/2012 | Suciu-Foca et al. | |
| 2003/0017143 A1 | 1/2003 | Suciu-Foca et al. | |
| 2003/0118997 A1 | 6/2003 | Benjanin et al. | |
| 2003/0165875 A1 | 9/2003 | Colonna et al. | |
| 2004/0048319 A1* | 3/2004 | Mather ............ | C07K 14/70503 435/7.23 |
| 2004/0241167 A1 | 12/2004 | Suciu-Foca et al. | |
| 2005/0250161 A1 | 11/2005 | Suciu-Foca et al. | |
| 2007/0041982 A1 | 2/2007 | Ponath et al. | |
| 2008/0038260 A1 | 2/2008 | Ponath et al. | |
| 2008/0175830 A1 | 7/2008 | Steinman et al. | |
| 2008/0311073 A1 | 12/2008 | Suciu-Foca et al. | |
| 2009/0070890 A1 | 3/2009 | Stassar | |

(Continued)

FOREIGN PATENT DOCUMENTS

| | | |
|---|---|---|
| WO | 1998/048017 | 10/1998 |
| WO | 1999/061085 | 12/1999 |

(Continued)

OTHER PUBLICATIONS

International Search Authority European Patent Office, "International Search Report and Written Opinion for PCT/US 2016042833", dated Feb. 1, 2019, pp. 19.

Bajorath, J., et al. 1995. Molecular model of the N-terminal receptor-binding domain of the human CD6 ligand ALCAM. Protein Sci 4: 1644-1647.

Balasa, B., et al., "CD40 ligand-CD40 interactions are necessary for the initiation of insulitis and diabetes in nonobese diabetic mice," J. Immunol., 1997, vol. 159, pp. 4620-4627, Publisher: The American Association of Immunologists Inc., Published in: http://www.jimmunol.org.

(Continued)

*Primary Examiner* — Lei Yao
(74) *Attorney, Agent, or Firm* — Beusse Wolter Sanks & Maire; Judith A. Evans; Timothy H. Van Dyke

(57) ABSTRACT

It has now been discovered that activated lymphocyte cell adhesion molecule (ALCAM)—also known as CD166—is the ligand of the innate immune receptor ILT3 that is expressed by DC and monocytes. It has been further discovered that the specific binding of ILT3 to its ligand CD166 on the surface of CD166-expressing cancer cells, arrested cancer cell growth and initiated apoptosis. Therefore, certain embodiments relate to methods and compositions for treating CD166-expressing cancers by administering ILT3Fc, full-length ILT3 or any CD166 ligand-binding fragment thereof.

5 Claims, 20 Drawing Sheets

Specification includes a Sequence Listing.

(56) References Cited

U.S. PATENT DOCUMENTS

| | | |
|---|---|---|
| 2009/0274685 A1 | 4/2009 | Suciu-Foca et al. |
| 2009/0202544 A1 | 8/2009 | Suciu-Foca et al. |
| 2009/0280109 A1 | 12/2009 | Sucio-Foca et al. |
| 2010/0086928 A1 | 4/2010 | Feinberg |
| 2010/0202973 A1 | 8/2010 | Pivarcsi et al. |
| 2011/0151580 A1 | 6/2011 | Diamandis |
| 2013/0156763 A1 | 6/2013 | Sucio-Foca et al. |
| 2013/0216476 A1 | 8/2013 | Boumsell |
| 2015/0110714 A1* | 4/2015 | Suciu-Foca ........ C07K 16/2803 424/1.49 |

FOREIGN PATENT DOCUMENTS

| | | | |
|---|---|---|---|
| WO | 2000/012103 | | 3/2000 |
| WO | 2000/068383 | | 11/2000 |
| WO | 03093443 | A2 | 11/2003 |
| WO | 2006/033811 | | 3/2006 |
| WO | 2006/119494 | | 3/2006 |
| WO | 2007/000671 | | 6/2006 |
| WO | 2007/089945 | | 2/2007 |
| WO | 2008117049 | A1 | 10/2008 |
| WO | 2009/104974 | | 2/2009 |
| WO | 2009/100955 | | 8/2009 |
| WO | 2010/056337 | | 5/2010 |
| WO | 2010/130351 | | 11/2010 |
| WO | 2011/066380 | | 11/2010 |
| WO | 2011/091270 | | 1/2011 |
| WO | 2011/009980 | | 3/2011 |
| WO | 2011/112719 | | 9/2011 |
| WO | 2013/033734 | | 3/2013 |
| WO | 2013/036282 | | 3/2013 |
| WO | 2013033734 | A1 | 3/2013 |
| WO | WO2013033734 | * | 3/2013 |
| WO | 2016/081643 | | 11/2015 |
| WO | 2016/179257 | | 5/2016 |
| WO | 2017/055540 | | 9/2016 |

OTHER PUBLICATIONS

Banchereau, J., et al., "Immunobiology of dendritic cells," Annu. Rev. Immunol., 2000, vol. 18, pp. 767-811, Publisher: Annual Reviews, Published in: http://www.ncbi.nlm.nih.gov/pubmed/10837075.

Baumjohann, D., et al. "MicroRNA-mediated regulation of T helper cell differentiation and plasticity." Nat Rev Immunol. Sep. 2013;13(9):666.

Beinhauer, B., et al., "Interleukin 10 regulates cell surface and soluble LIR-2 (CD885d) expression on dendritic cells resulting in T cell hyporesponsiveness in vitro," Eur. J. Immunol., 2004, vol. 34, pp. 74-80, Publisher: WILEY-VCH Verlag GmbH & Co, Published in: http://www.ncbi.nlm.nih.gov/pubmed/14971032.

Bisikirska, B., et al., "TCR Stimulation with Modified anti-CD3 mAB expands CD8+ T cell population and induces CD8+ T cell population and induces CD8+CD25+ Tregs," J. Clin. Invest., 2005, vol. 115: pp. 2904-2913, Publisher: American Society for Clinical Investigation, Published in: http://www.ncbi.nlm.nih.gov/pmc/articles/PMC1201661/.

Bluestone, Ja, et al. "The functional plasticity of T cell subsets." Nat Rev Immunol. 2009;9:811.

Bowen, M.A., et al. 1995. "Cloning, mapping, and characterization of activated leukocyte-cell adhesion molecule (ALCAM), a CD6 ligand." J Exp Med 181: 2213-2220.

Bruder, S. P., et al.1998. Mesenchymal stem cell surface antigen SB-10 corresponds to activated leukocyte cell adhesion molecule and is involved in osteogenic differentiation. J Bone Miner Res 13: 655-663.

Cella, M., et al., "A novel inhibitory receptor (ILT3) expressed on monocytes, macrophages, and dendritic cells involved in antigen processing," J. Exp. Med., 1997, vol. 185, pp. 1743-1751, Publisher: The Rockefeller University Press, Published in: http://jem.rupress.org/.

Chang, C., et al., "Tolerization of dendritic cells by T(S) cells: the crucial role of inhibitory receptors ILT3 and ITL4," Jan. 28, 2002. Nature Immunology, vol. 23, pp. 237-243, Publisher: Nature Publishing Group, Published in: http://www.nature.com/ni/journal/v3/n3/abs/ni760.html.

Chang, C., et al., "Polymorphism and linkage disequilibrium of immunoglobulin-like transcript 3 gene," Human Immunology, Jan. 18, 2008. pp. 284-290, vol. 69, Published by Elsevier, Inc.

Chang, C., et al. "Ig-Like Transcript 3 regulates expression of proinflammatory cytokines and migration of activated T cells." Journal of Immunology, 2009. vol. 182, p. 5208.

Chang, C., et al., "BCL6 Is Required for Differentiation of Ig-Like Transcript 3-FC Induced CD8+ T Suppressor Cells," Oct. 8, 2010. Journal of Immunology, vol. 185, pp. 5714-5722.

Chang, C., et al. "Downregulation of Inflammatory microRNAs by Ig-like Transcript 3 is essential for the differentiation of human CD8(+) T suppressor cells." Journal of Immunology. 2012, vol. 188, p. 3042.

Chen, L., et al., "Allospecific CD8 T suppressor cells induced by multiple MLC stimulation or priming in the presence of ILT3.Fc have similar gene expression profile." Human Immunology, 2014, pp: 190-196, vol. 75, Published by: Elsevier.

Ciubotariu, R., et al., "Persistent allopeptide reactivity and epitope spreading in chronic rejection of organ allografts," J. Clin. Invest., 1998, vol. 101, pp. 398-405, Publisher: The American Society for Clinical Investigation, Inc., Published in: http://www.jci.org/articles/view/1117/files/pdf.

Ciubotariu, R., et al., "Specific suppression of human CD4+ Th cell responses to pig MHC antigens by CD8+ CD28 regulatory T cells," J Immunol., 1998, vol. 161, pp. 5193-5202, Publisher: The American Assoc. of Immunologists, Inc., Published in: http://www.jimmunol.org/content/161/10/5193.full.

Ciubotariu, R., et al., "Detection of T suppresor cells in patients with organ allografts," Hum. Immunol., 2001, vol. 62, pp. 15-20, Publisher: Elsevier, Published in: http://www.ncbi.nlm.nih.gov/pubmed/11165711.

Colonna, M., et al., "Cutting edge: human myelomonoytic cells express an inhibitory receptor for classical and nonclassical MHC class I molecules," J. Immunol., (1998), vol. 160, pp. 3096-3100, Publisher: The American Association of Immunologists, Inc., Published in: http://www.jimmunol.org/content/160/7/3096.full.

Colonna, M., et al., "A novel family of Ig-like receptors for HLA class I molecules that modulate function of lymphoid and myeloid cells," J. Leukoc. Biol., 1999, vol. 66, pp. 375-381, Publisher: The Society for Leukocyte Biology, Published in: http://www.ncbi.nlm.nih.gov/pubmed/10496306.

Colonna, M., et al., "A family of inhibitory and activating Ig-like receptors that modulate function of lymphoid and myeloid cells," Semin. Immunol., 2000, vol. 12, pp. 121-127, Publisher: Elsevier, Published in: http://www.ncbi.nlm.nih.gov/pubmed/10496306.

Colovai, A., et al., "Induction of xenoreactive CD4 T-cell anergy by suppressor CD8+ CD28 T cells," Transplantation, 2000, vol. 69, pp. 1304-1310, Publisher: Ovid Technologies, Inc., Published in: http://www.ncbi.nlm.nih.gov/ pubmed/10798745.

Colovai, A.I., et al., "Expression of Inhibitory Receptor ILT3 on Neoplastic B Cells is Associated with Lymphoid Tissue Involvement in Chronic Lymphocytic Leukemia." Cytometry Part B (Clinical Cytometry). Jan. 31, 2007, vol. 72B, pp. 354-362.

Cotner, T., et al., "Simultaneous flow cytometric analysis of human T cell activation antigen expression and DNA content," J. Exp. Med., 1983, vol. 157, pp. 461-472, Publisher: The Rockefeller University Press, Published in: http:/jem.rupress.org/content/157/2/461.abstract.

Damle, N., et al., "Alloantigen-specific cytotoxic and suppressor T lymphocytes are derived from phenotypically distinct precursors," J. Immunol., 1983, vol. 131, pp. 2296-2300, Publisher: The American Association of Immunologists Inc., Published in: http://www.ncbi.nlm.nih.gov/pubmed/6195259.

Daniels, TR., et al. "Transferrin Receptors and the Targeted Delivery of Therapeutic Agents Against Cancer," Biocim Biophys Acta. Mar. 2012; 1820(3); pp. 291-317.

(56) References Cited

OTHER PUBLICATIONS

Daniels-Wells, TR., et al. "Efficacy of an Anti-transferrin Receptor 1 antibody Against AIDS-Related Non-Hodgkin Lymphoma: A Brief Communication," Journal of Immunotherapy, Oct. 2015. vol. 38 / Issue 8. pp. 307-310.
Davalli, A., et al., "Vulnerability of islets in the immediate post-transplantation period: Dynamic changes in structure and function," Diabetes, 1996, vol. 45, pp. 1161-1167, Publisher: The American Diabetes Association, Published in: http://www.ncbi.nlm.nih.gov/pubmed/8772716.
Dhodapkar, M., et al., "Antigen-specific inhibition of effector T cell function in humans after injection of immature dendritic cells," J. Exp. Med., 2001, vol. 93, pp. 233-238, Publisher: The Rockefeller University Presshttp://jem.rupress.org/content/193/2/233.abstract.
"Dobrowolska, H., et al., ""Expression of Immune Inhibitory Receptor ILT3 in Acute Myeloid Leukemia with Monocytic Differentiation,"" Cytometry Part B: Clinical Cytometry, 2013, pp. 21-29, vol. 84B, No. 1, Publisher: John Wiley & Sons Inc."
Expert Opinion Ther. Patents, "CD47-Fc Fusion Proteins as Putative Immunotherapeutic Agents for the Treatment of Immunological and Inflammatory Disease," Expert Opinion on Therapeutic Patents, 2008, vol. 18, pp. 555-561, Publisher: Informa Healthcare, Published in: http://www.ingentaconnect.com/content/apl/etp/2008/00000018/00000005/art00008.
Fabbri, M., et al., "MicroRNAs bind to Toll-like receptors to induce prometastatic inflammatory response." Proc Natl Acad Sci USA, 2012. vol. 109, p. E2110.
Garcia-Alonso, A., et al., "CD28 expression on peripheral blood T lymphocytes after orthotopic liver transplant: upregulation in acute rejection," Hum. Immunol., 1997, vol. 53, pp. 64-72, Publisher: Elsevier, Published in: http://www.ncbi.nlm.nih.gov/pubmed/?term=CD28+expression+on+peripheral+blood+T+lymphocytes+after+orthotopic+liver+transplant%3A++upregulation+in+acute+rejection.
Gaziel-Sovran, A., et al, "miR-30b/30d regulation of GalNAc transferases enhances invasion and immunosuppression during metastasis." Cancer Cell. 2011, vol. 20, p. 104.
Gillespie, K., et al., "Type 1 Diabetes: pathogenesis and prevention," CMAJ, 2006, vol. 175: pp. 165-170, Publisher: CMA Media Inc., Published in: http://www.ncbi.nlm.nih.gov/pubmed/16847277.
Gregori, S., et al., "An anti-CD45RO/RB monoclonal antibody modulates T cell responses via induction of apoptosis and generation of regulatory T cells," J. Exp. Med., 2005, vol. 201, pp. 1293-1305, Publisher: The Rockefeller University Press, Published in: http://www.jem.rupress.org.
Groux, H., et al., "A CD4+ T-cell subset inhibits antigen-specific T-cell responses and prevents colitis," Nature, 1997, vol. 89, pp. 737-742, Publisher: Nature Publishing Group, Published in: http://www.nature.com/nature/journal/v389/ n6652/full/389737a0.html.
Guo, H., et al., "Mammalian microRNAs predominantly act to decrease target mRNA levels." Nature 2010;466:835-40.
Gutierrez-Vazquez, C., et al., "Transfer of extracellular vesicles during immune cell-cell interactions." Immunol Rev 2013;251:125.
Haars, R., et al., "Modulation of T-cell antigen receptor on lymphocyte membrane," Immunogenetics, 1984, vol. 20, pp. 397-405, Publisher: Springer, Published in: http://www.ncbi.nlm.nih.gov/pubmed/6333390.
Hoffman-Fezer, G., et al "Immunohistology and immunocytology of human T-cell chimerism and graft-versus-host disease in SCID mice," Blood, 1993, vol. 81, pp. 3440-3448, Publisher: The American Society of Hematology, Published in: http://www.bloodjournal.org.
Huffaker, TB, et al. "Epistasis between microRNAs 155 and 146a during T cell-mediated antitumor immunity." Cell Rep, 2012, vol. 2 p. 1697.
IB, "International Search Report and Written Opinion for Corresponding International Application No. PCT/US2012/53714", dated Jan. 18, 2013, pp. 1-16, Publisher: WIPO.
IB, "International Search Report and Written Opinion for Corresponding International Application No. PCT/US2016/042833", dated Oct. 7, 2016, pp. 1-10, Publisher: WIPO.

Jenkins, M., et al., "Antigen presentation by chemically modified splenocytes induces antigen-specific T cell unresponsiveness in vitro and in vivo," J. Exp. Med., 1987, vol. 165: pp. 302-319, Publisher: The Rockefeller University Press, Published in: http://www.ncbi.nlm.nih.gov/pmc/articles/PMC2188516/.
Jiang, S., et al., "Induction of MHC-class I restricted human suppressor T cells by peptide priming in vitro," Hum. Immunol., 1998, vol. 59, pp. 690-699, Publisher: Elsevier, Published in: http://www.ncbi.nlm.nih.gov/pubmed/9796737.
Jonuleit, H., et al., "Identification and functional characterization of human CD4(+)CD25(+) T cells with regulatory properties isolated from peripheral blood," J. Exp. Med., 2001, vol. 193, No. 11, pp. 1285-1294, Publisher: The Rockefeller University Press, Published in: http://www.ncbi.nlm.nih.gov/pmc/articles/PMC2193380/.
Jonuleit, H., et al., "Induction of Interleukin 10-Producing, Nonproliferating Cd4+ T Cells with Regulatory Properties by Repetitive Stimulation with Allogeneic Immature Human Dendritic Cells," Journal of Experimental Medicine, 2001, pp. 1213-1222, vol. 192, No. 9.
Kanki, J. P., S. Chang, and J. Y. Kuwada. 1994. The molecular cloning and characterization of potential chick DM-GRASP homologs in zebrafish and mouse. J Neurobiol 25: 831-845.
Kaufman, D., et al. "Clinical Islet Transplantation", Current Diabetes Reports. 2003, vol. 3, pp. 344-350. Copyright 2003 by Current Science, Inc.
Kim-Schulze, S., et al., "Recombinant Ig-Like Transcript 3-Fc Modulates T Cell Responses via Induction of Th Anergy and Differentiation of CD8+ T Suppressor Cells," J. Immunol., 2006, vol. 176, pp. 2790-2798, Publisher: The American Association of Immunologists, Inc., Published in: http://www.jimmunol.org/content/176/5/2790.full.
Klein, D., et al., "A functional CD40 receptor is expressed in pancreatic beta cells," Diabetologia, 2005, vol. 48, pp. 268-276, Publisher: Springer-Vailag, Published in: http://link.springer.com/article/10.1007%2Fs00125-004-1645-7.
Lang, R., et al., "DUSP meet immunology: dual specificity MAPK phosphatases in control of the inflammatory response." J Immunol 2006;177:7497-504.
Lanzavecchia, A., "Immunology. License to Kill," Nature, 1998, vol. 393, pp. 413-414, Publisher: Nature Publishing Group, Published in: http://www.ncbi.nlm.nih.gov/pubmed/9623994.
Lechler, R., et al., "Dendritic cells in transplantation—friend or foe?," Immunity, 2001, vol. 14, pp. 357-368, Publisher: Elsevier, Published in: http://www.ncbi.nlm.nih.gov/pubmed/11336681.
Leoh, LS, et al., "Gene Delivery in Malignant B Cells Using the Combination of Lentiviruses Conjugated to Anti-Transferrin Receptor Antibodies and an Immunoglobulin Promoter," Journal of Gene Medicine, Jan./Feb. 2014. vol. 16 / Issue 1-2., pp. 11-27.
Leukocyte Immunoglobulin-like Receptor, Subfamily B. Member 4; LILRB4, OMIM 604821 (2000).
Li, J, et al., "T suppressor lymphocytes inhibit NFKB-mediated transcription of CD86 gene in APC," J. Immunol., 1999, vol. 163, pp. 6386-6392, Publisher: The American Association of Immunologists, Inc., Published in: http://www. jimmunol.org/content/163/12/6386.short.
Liston, A., et al.,"Dicer-dependent microRNA pathway safeguards regulatory T cell function." J Exp Med 2008;205:1993-2004.
Liu, Z., et al., "Specific suppression of T helper alloreactivity by allo-MHC class I-restricted CD8+ CD28− T cells," Int. Immunol., 1998, vol. 10, pp. 775-783, Publisher: Oxford University Press, Published in http://www.ncbi.nlm.nih.gov/ pubmed/9678758.
Liu, Z., et al., "Inhibition of CD40 signaling pathway in antigen presenting cells by T suppressor cells," Hum. Immunol., 1999, vol. 60, pp. 568-574, Publisher: Elsevier, Published in: http://www.sciencedirect.com/science/article/pii/ S0198885999000440.
"Loisel, S., et al. ""Antitumour effects of single or combined monoclonal antibodies directed against membrane antigens expressed by human B cells leukaemia,"" Molecular Cancer, Apr. 2011. vol. 10, p. 42".
Lopez-Pedrera, C., et al. "Proteomic analysis of acute myeloid leukemia: Identification of potential early biomarkers and therapeutic targets," Proteomics, vol. 6, Issue 51, pp. S293-S299; 2006.
Lu, H., et al. "Leukocyte Ig-like receptor B4 (LILRB4) is a potent inhibitor of FcgRI-mediated monocyte activation via dephosphorylation

(56) References Cited

OTHER PUBLICATIONS of multiple kinases," Journal of Experimental Medicine, vol. 185, Issue 10, pp. 1743-1751 Dec. 11, 2009.
Lutz, M., et al., "Immature denditric cells generated with low doses of GM-CSF in the absence of IL-4 are maturation resistant and prolong allograft survival in vivo," Eur. J. Immunol., 2000, vol. 30, pp. 1813-1822, Publisher: WILEY-VCH Verlag GmbH & Co, Published in http://www.ncbi.nlm.nih.gov/pubmed/10940870.
Manavalan, J., et al., "High expression of ILT3 and ILT4 is a general feature of tolerogenic dendritic cells," Transplant Immunology, 2003, vol. 11, pp. 245-258, Publisher: Elsevier, Published in: http://www.sciencedirect.com/science/article/pii/S0966327403000583.
Matsumoto, A. et al.,1997. Cloning and characterization of HB2, a candidate high density lipoprotein receptor. Sequence homology with members of the immunoglobulin superfamily of membrane proteins. The Journal of biological chemistry 272: 16778-16782.
Mingari, M., et al., "Human CD8+ T lymphocytes subsets that express HLA class I-specific inhibitory receptors represent oligoclonally or monoclonally expanded cell populations," PNAS, 1996, vol. 93, pp. 12433-12438, Publisher: National Academy of Sciences, Published in: http://www.ncbi.nlm.nih.gov/pmc/articles/PMC38009/.
Mingari, M., et al., "Regulation of KIR expression in human T cells: A safety mechanism that may impair protective T-cell responses," Immunol. Today, 1998, vol. 19, pp. 153-157, Publisher: Elsevier, Published in: http://www.sciencedirect.com/science/article/pii/S016756999701236X.
Mittelbrunn, M., et al."Unidirectional transfer of microRNA-loaded exosomes from T cells to antigen-presenting cells." Nat Commun 2011;2:282.
"Nagai, K., et al., ""Development of a complete human anti-human transferrin receptor C antibody as a novel marker of oral dysplasia and oral cancer,"" Cancer Medicine. Aug. 2014, vol. 3 / Issue 4., pp. 1085-1099".
Penna, G., et al. "Expression of the Inhibitory Receptor ILT3 on dendritic cells is dispensable for induction of CD4+Foxp3+ regulatory T cells y 1,25-dihydroxyvitamin D3," Blood. Nov. 15, 2005. vol. 106 / Issue 10. pp. 3490-3497.
Pham, et al. "Gene-Expression Profiling for Rejection Surveillance after Cardiac Transplantation," New England Journal of Medicine. vol. 362 / Issue 20, p. 1890. 2010.
Phillips, N., et al., "Blockade of CD40-mediated signaling is sufficient for inducing islet but not skin transplantation tolderance," J. Immunol., 2003, vol. 170, pp. 3015-3023, Publisher: The American Association of Immunologists, Inc.., Published in: http://www.jimmunol.org.
Pipkin, Me., et al. "Interleukin-2 and inflammation induce distinct transcriptional programs that promote the differentiation of effector cytolytic T cells " Immunity 2010;32:79.
Przepiorka, D., et al., "Risk Factors for Acute Graft-Versus-Host Disease After Allogeneic Blood Stem Cell Transplantation," Blood, 1999, pp. 1465-1470, vol. 94, No. 4.
Qin, H., et al., "CD8+ suppressor and cytotoxic T cells recognize the same human leukocyte antigen-A2 restricted cytomegalovirus peptide," Human Immunology, 2008, pp. 776-80, vol. 69, No. 11, Publisher: Elsevier Inc., Published in: https://www.ncbi.nlm.nih.gov/pubmed/18848854.
Ravetch, J., et al., "Immune inhibitor receptors," Science, 2000, vol. 290, pp. 84-88, Publisher: AAAS, Published in: http://www.ncbi.nlm.nih.gov/pubmed/11021804.
Rea, D., et al., "Glucocorticoids transform CD40-triggering of dendritic cells into an alternative activation pathway resulting in antigen-presenting cells that secrete IL-10," Blood, 2000, vol. 95, pp. 3162-3167, Publisher: American Society of Hematology, Published in: http://bloodjournal.hematologylibrary.org/content/95/10/3162.long.
Roncarolo, M., et al., "Differentiation of T regulatory cells by immature dendritic cells," J. Exp. Med., 2001, vol. 193, pp. F5-F9, Publisher: The Rockefeller University Press, Published in: http://jem.rupress.org/content/193/2/F5.long.

Roth, A., et al. "Anti-CD166 Single Chain Antibody-mediated Intracellular Delivery of Liposomal drugs to prostate cancer cells." Molecular Cancer Therapeutics. vol. 10, pp. 2737-2746, Oct. 2007.
Sakaguchi, S., et al "Immunologic self-tolerance maintained by activated T cells expressing IL-2 receptor alpha-chains (CD25). Breakdown of a single mechanism of self-tolerance causes various autoimmune diseases," J. Immunol. 155: 1151-1164 (1995).
Sakaguchi, S., "Regulatory T cells: Key controllers of immunologic self-tolerance," Cell, 2000, vol. 101, pp. 455-458, Publisher: Elsevier, Published in: http://www.ncbi.nlm.nih.gov/pubmed/10850488.
Samra, E. Bou, et al. "Development of gene expression-based risk score in cytogenetically normal acute myeloid leukemia patients," Oncotarget, Vo. 3, Issue 8; Aug. 2012.
Sawant, DV., et al., "The Bc16 target gene microRNA-21 promotes Th2 differentiation by a T-cell intrinsic pathway." Molecular Immunology, 2013. vol. 54, p. 435.
Schwartz, R., et al., "Models of T cell anergy: is there a common molecular mechanism?," J. Exp. Med., 1996, vol. 184, pp. 1-8, Publisher: The Rockefeller University Press, Published in: http://www.ncbi.nlm.nih.gov/pmc/articles/ PMC2192660/.
Shevach, E., et al., "Regulatory T cells in autoimmunity," Annu. Rev. Immunol., 2000, vol. 18, pp. 423-449, Publisher: Annual Reviews, Published in: http://www.ncbi.nlm.nih.gov/pubmed/10837065.
Steinman, R., et al., "The dendritic cell system and its role in immunogenicity," Annu. Rev. Immunol., 1991, vol. 9, pp. 271-296, Publisher: Annual Reviews, Published in: http://www.ncbi.nlm.nih.gov/pubmed/1910679.
Steinman, R., et al., "The induction of tolerance by dendritic cells that have captured apoptotic cells," J. Exp. Med., 2000, vol. 191, pp. 411-416, Publisher: The Rockefeller University Press, Published in: http://www.ncbi.nlm.nih.gov/ pmc/articles/PMC2195815/.
Suciu-Foca, N., et al., "A late-differentiation antigen associated with the helper inducer function of human T cells," Nature, 1985, vol. 318, pp. 465-467, Publisher: Nature Publishing Group, Published in: http://www.ncbi.nlm.nih.gov/pubmed/?term=A+late-differentiation+antigen+associated+with+the+helper+inducer+function+of+human+T+cells.
Suciu-Foca, N., et al., "Idiotypic network regulations of the immune response to HLA," Transplantation Proceedings, 1985, vol. 17, No. 1, pp. 716-719, Publisher: Elsevier, Published in: http://www.journals.elsevier.com/transplantation-proceedings/.
Suciu-Foca, N., et al., "Distinct mRNA microarray profiles of tolerogenic dendritic cells," Hum. Immunol., 2001, vol. 62, pp. 1065-1072, Publisher: Elsevier, Published in: http://www.ncbi.nlm.nih.gov/pubmed/?term=Distinct+mRNA+microarray+profiles+of+tolerogenic+dendritic+cells%2C%22+Hum.+Immunol.%2C+2001%2C+Vol.+62%2C+pp.+1065-1072.
Suciu-Foca, N., et al., "Central role of ILT3 in the T suppressor cell cascade," Cellular Immunology, 2007, vol. 248, pp. 59-67, Publisher: Elsevier, Published in: http://www.ncbi.nlm.nih.gov/pubmed/17923119.
Suciu-Foca, N., et al., "Soluble Ig-like transcript 3 inhibits tumor allograft rejection in humanized SCID Mice and T cell responses in cancer patients," J. Immunol., 2007, vol. 178, pp. 7432-7441, Publisher: The American Association of Immunologists, Inc., Published in: http://www.jimmunol.org/content/178/11/7432.full.
Suciu-Foca, N., et al., "Molecular characterization of allospecific T suppressor and tolerogenic dendritic cells: review," International Immunopharmacology, 2005, pp. 2-11, vol. 5, No. 1, Publisher: Elsevier Inc, Published in: https://www.ncbi.nlm.nih.gov/pubmed/15589454.
Takahashi, T., et al "Immunologic self-tolerance maintained by CD25+ CD4+ regulatory T cells constitutively expressing cytotoxic T lymphocyte-associated antigen 4," J. Exp. Med., 2000, vol. 192, pp. 303-310, Publisher: The Rockefeller University Press, Published in: http://www.jem.org.
Tzanchanis, D., et al., "Tob is a negative regulator of activation that is expressed in anergic and quiescent T cells." Nat Immunol 2001;2:1174-82.
Tzanchanis, D., et al., "Twisted gastrulation (Tsg) is regulated by Tob and enhances TGF-beta signaling in activated T lymphocytes." Blood 2007;109:2944-52.

(56) References Cited

OTHER PUBLICATIONS

Van Kempen, L.C., et al., 2001. Molecular basis for the homophilic activated leukocyte cell adhesion molecule (ALCAM)-ALCAM interaction. The Journal of biological chemistry 276: 25783-25790.

Vlad, G., et al., "License to heal: bidirectional interaction of antigen-specific regulatory T cells and tolerogenic APC," J. Immunol., 2005, vol. 174, pp. 5907-5914, Publisher: The American Association of Immunologists Inc., Published in: http://www.jimmunol.org.

Vlad, G., et al "Immunosuppressive Activity of Recombinant ILT3," International Immunopharmacology. Aug. 24, 2006, vol. 6, Issue 13-14, pp. 1889-94, Published by: Elsevier Inc.

Vlad, G., et al "Immunoglobulin-Like Transcrip 3-Fc Suppresses T-Cell Responses to Allogeneic Human Islet Transplants in hu-NOD/SCID Mice," Diabetes. vol. 57, pp. 1878-1886. Jul. 2008.

Vlad, G., et al. "Suppression of xenogeneic graft-versus-host disease by treatment with immunoglobulin-like transcript 3-Fc." Hum Immunol. vol. 70 / Issue 9, pp. 663-669, Sep. 2009.

Vlad, G., et al., "Gene profile analysis of CD8(+) ILT3-Fc induced T suppressor cells." Human Immunology, 2011, vol. 72, pp. 107-114, Published by: Elsevier Inc.

Vlad, G., et al. "Membrane and soluble ILT3 are critical to the generation of T suppressor cells and induction of immunological tolerance." Int. Rev. Immunolgy, 2010, vol. 29, Issue 2, pp. 119-132, Published by: Taylor and Francis Ltd.

Vlad, G., et al., "Induction of antigen-specific human T suppressor cells by membrane and soluble ILT3," Experimental and Molecular Pathology, 2012, pp. 294-301, vol. 93, No. 3, Publisher: Elsevier Inc., Published in: https://www.ncbi.nlm.nih.gov/pubmed/23018130.

Waldmann, T.A., et al. "Phase 1 trial of IL-15 trans presentation blockade using humanized Mikβ1 mAb in patients with T-cell large granular lymphocytic leukemia," Blood, Jan. 2013. vol. 121/Issue 3, pp. 476-484.

Wang, D., et al., "A single amino acid determines lysophospholipid specificity of the S1P1 (EDG1) and LPA1 (EDG2) phospholipid growth factor receptors," The Journal of Biological Chemistry, 2001, vol. 276, 49213-49220, Publisher: American Soc. for Biochemistry and Molecular Biology, Published in: http://www.ncbi.nlm.nih.gov/pubmed/11604399.

Wang, G., et al. "Serum and urinary cell-free MiR-146a and MiR-155 in patients with systemic lupus erythematosus," Journal of Rheumotology. 2010, vol. 37, p. 2516.

Wang, S., et al. "MicroRNA-146a feedback suppresses T cell immune function by targeting Stat1 in patients with chronic hepatitis B." Journal of Immunology. 2013. vol. 191, p. 293.

Weidle, U.H., et al., 2010. ALCAM/CD166: cancer-related issues. Cancer Genomics Proteomics 7: 231-243.

Whisstock, J., et al., "Prediction of protein function from protein sequence and structure," Quarterly Review of Biophysics, 2003, vol. 36, pp. 307-340, Publisher: Cambridge University Press, Published in: http://www.ncbi.nlm.nih.gov/pubmed/15029827.

Wiiger, MT, et al. "A novel human recombinant single-chain antibody targeting CD166/ALCAM inhibits cancer cell invasion in vitro and in vivo tumor growth." Cancer Immunology Immunotherapy, vol. 59 / Issue 11, Nov. 2010, pp. 1665-1674.

Xu, Z., et al., "MiR-365, a novel negative regulator of interleukin-6 gene expression, is cooperatively regulated by Sp1 and NF-kappaB." J Biol Chem 2011;286:21401.

Xu, Z., et al., "ILT3.Fc inhibits the production of exosomes containing inflammatory microRNA in supernatants of alloactivated T cells," Human Immunology, 2014, pp. 756-59, vol. 75, No. 8, Publisher: Elsevier Inc., Published in: https://www.ncbi.nlm.nih.gov/pubmed/24862932.

Yang, L., et al. "MIR-146a Controls the Resolution of T Cell Responses in Mice," Journal of Experimental Medicine, 2012, vol. 209, p. 1655.

"Yoshida, K., et al., ""Bcl6 controls granzyme B expression in effector CD8+ T cells,"" European Journal of Immunology, 2006, pp. 3146-56, vol. 36, No. 12, Publisher: Wiley-VCH Verlag GmbH & Co., Published in: https://www.ncbi.nlm.nih.gov/pubmed/17125145".

"Yu, D., et al., ""The Transcriptional Repressor Bcl-6 Directs T Follicular Helper Cell Lineage Commitment,"" Immunity, 2009, pp. 457-68, vol. 39, No. 3, Publisher: Elsevier.Inc., Published in: https://www.ncbi.nlm.nih.gov/pubmed/19631565".

"Zhou, X., et al., ""Selective miRNA disruption in T reg cells leads to uncontrolled autoimmunity,"" The Journal of Experimental Medicine, 2008, pp. 1983-1991, vol. 205, No. 9, Publisher: Rockefeller University Press Published in: https://www.ncbi.nlm.nih.gov/pubmed/18725525".

Zotova, E., et al., "Inflammation in Alzheimer's disease: relevance to pathogenesis and therapy," Alzeheimer's Research & Therapy, 2010, pp. 1-9. vol. 2, No. 1, Publisher: BioMed Central, Published in: https://www.ncbi.nlm.nih.gov/pubmed/20122289.

International Search Report and Written Opinion, International Patent Application No. PCT/US2016/042833, dated Oct. 7, 2016, pp. 1-10.

Chan and Carter, Therapeutic antibodies for autoimmunity and inflammation, Nature Reviews Immunology, 2010, pp. 301-316, vol. 10.

Marcucci, F., et al., Antibody-Drug Conjugates (ADC) Against Cancer Stem-Like Cells(CSC)—Is There Still Room or Optimism?, Frontiers in Oncology, 2019, vol. 9, Article 167.

Cheng, H., et al., Crystal Structure of Leukocyte Ig-like Receptor LILRB4, J. Biol. Chem., 2011, pp. 18013-18025, vol. 286.

* cited by examiner

|  | ILT3Fc-FITC | | CD166-PE | |
|---|---|---|---|---|
|  | w/o ILT3Fc | w/w ILT3Fc | w/o ILT3Fc | w/w ILT3Fc |
| Control Treatment | 1.08% | 0.80% | 1.23% | 1.08% |
| PWM(0.05ug/ml) | 23.24% | 15.17% | 16.60% | 10.58% |
| CD3/CD28(5ug/ml,1ug/ml) | 26.89% | 20.35% | 27.17% | 17.97% |

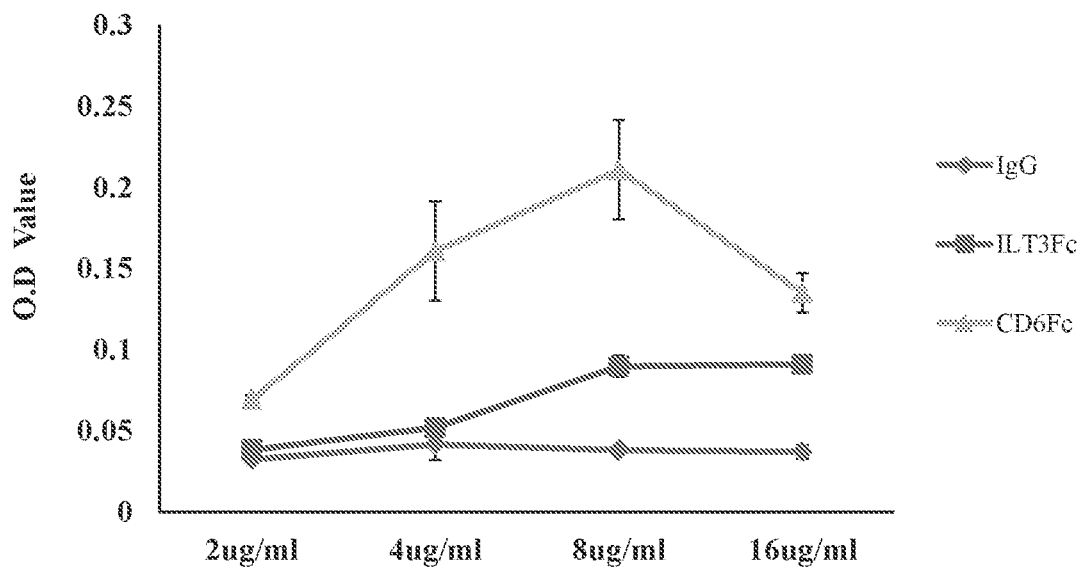
FIG. 5A  Recombinant CD166 binding to coated Protein ELISA
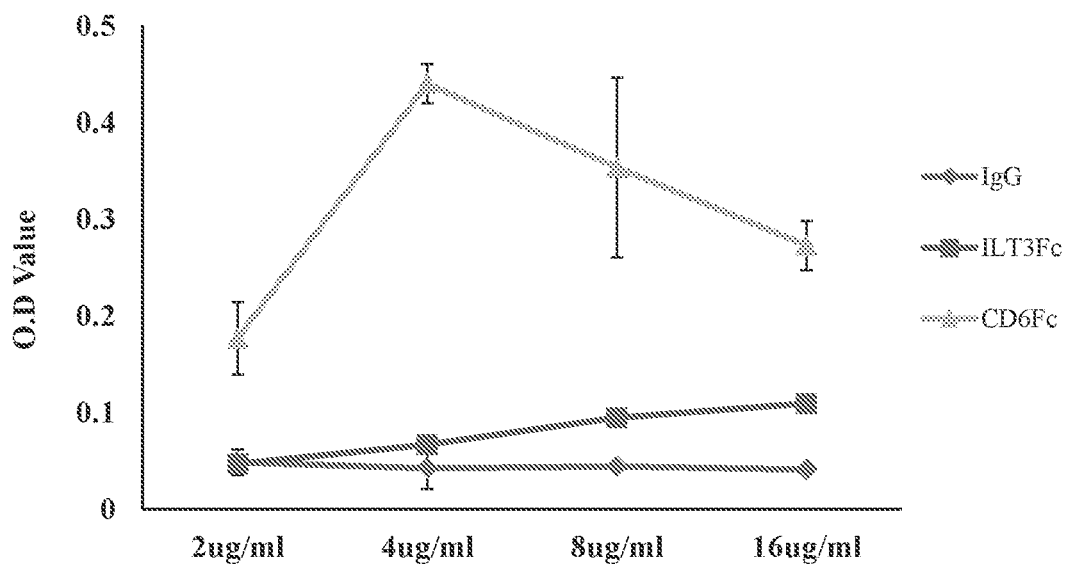
FIG. 5B  CD166-Fc binding to coated Protein detected by ELISA 36 Hours Post Treatment
2-23-15

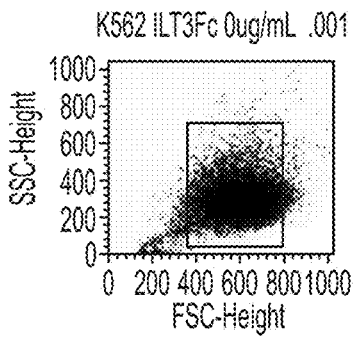

Sample ID: K562 ILT3Fc 0ug/mL
Acquisition Date: 23-Feb-15
Gate:G1
Gated Events: 12009
Total Events: 12777

| Marker | Events | %Gated | %Total |
|---|---|---|---|
| All | 12009 | 100.00 | 93.99 |
| M1 | 10381 | 86.44 | 81.25 |

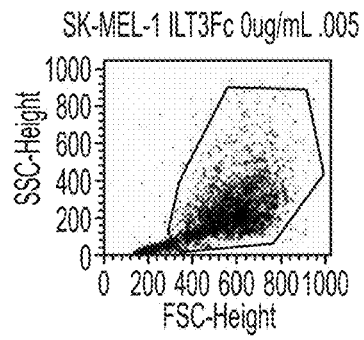

Sample ID: SK-MEL-1 ILT3Fc 0ug/mL
Acquisition Date: 23-Feb-15
Gated Events: 20845
Total Events: 24335

| Marker | Events | %Gated | %Total |
|---|---|---|---|
| All | 20845 | 100.00 | 85.66 |
| M1 | 11156 | 53.52 | 45.84 |

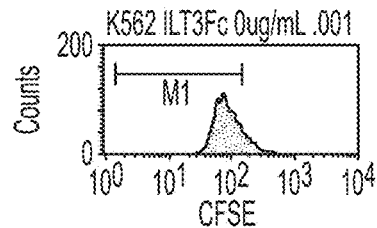

Sample ID: K562 ILT3Fc 50ug/mL
Acquisition Date: 23-Feb-15
Gate:G1
Gated Events: 10433
Total Events: 10811

| Marker | Events | %Gated | %Total |
|---|---|---|---|
| All | 10433 | 100.00 | 96.50 |
| M1 | 2705 | 25.93 | 25.02 |

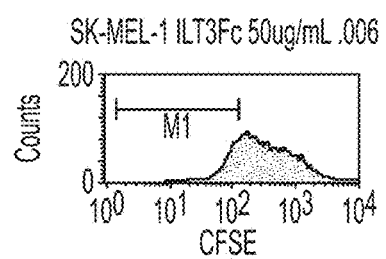

Sample ID: SK-MEL-1 ILT3Fc 50ug/mL
Acquisition Date: 23-Feb-15
Gated Events: 20983
Total Events: 25187

| Marker | Events | %Gated | %Total |
|---|---|---|---|
| All | 20983 | 100.00 | 83.31 |
| M1 | 4752 | 22.65 | 18.87 |

FIG. 6C

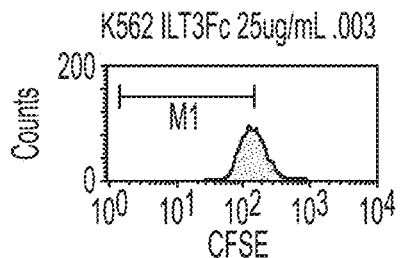

Sample ID: K562 ILT3Fc 25ug/mL
Acquisition Date: 23-Feb-15
Gate: G1
Gated Events: 10338
Total Events: 10665

| Marker | Events | %Gated | %Total |
|---|---|---|---|
| All | 10338 | 100.00 | 96.93 |
| M1 | 5910 | 57.17 | 55.41 |

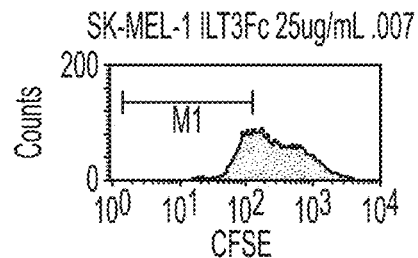

Sample ID: SK-MEL-1 ILT3Fc 25ug/mL
Acquisition Date: 23-Feb-15
Gated Events: 20927
Total Events: 24977

| Marker | Events | %Gated | %Total |
|---|---|---|---|
| All | 20927 | 100.00 | 83.79 |
| M1 | 5430 | 25.95 | 21.74 |

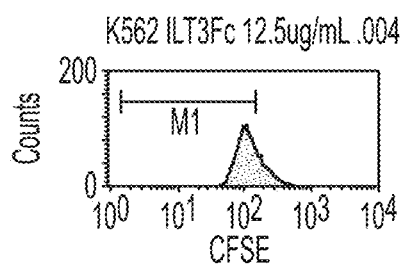

Sample Id: K562 ILT3Fc 12.5ug/ml
Acquisition Date: 23-Feb-15
Gate: G1
Gated Events: 10448
Total Events: 10835

| Marker | Events | %Gated | %Total |
|---|---|---|---|
| All | 10448 | 100.00 | 96.43 |
| M1 | 8029 | 76.85 | 74.10 |

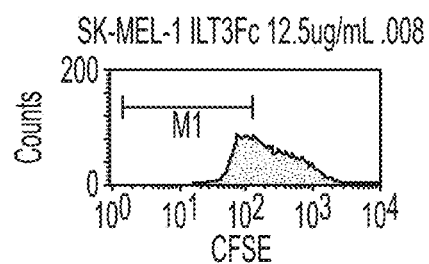

Sample ID: SK-MEL-1 ILT3Fc 12.5ug/mL
Acquisition Date: 23-Feb-15
Gated Events: 20918
Total Events: 24712

| Marker | Events | %Gated | %Total |
|---|---|---|---|
| ALL | 20918 | 100.00 | 84.65 |
| M1 | 7113 | 34.00 | 28.78 |

FIG. 6C
CONTINUED

ILT3Fc inhibits Tumor cell growth based on a 72 hour assay
*(Cell Numbers counted with Trypan-Blue exclusion method)*
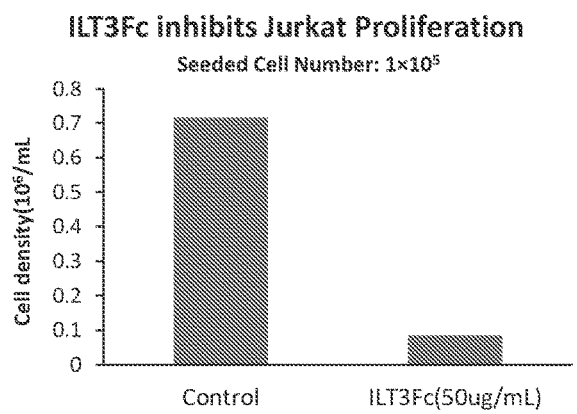
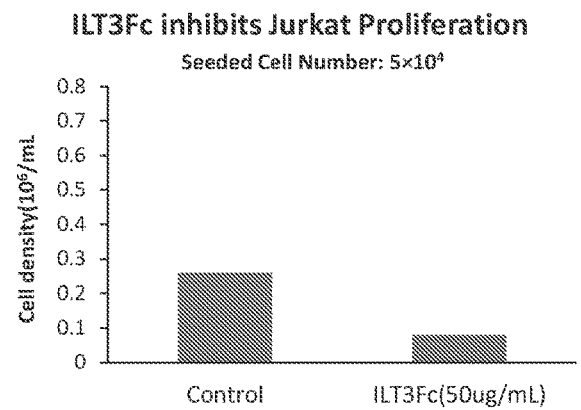
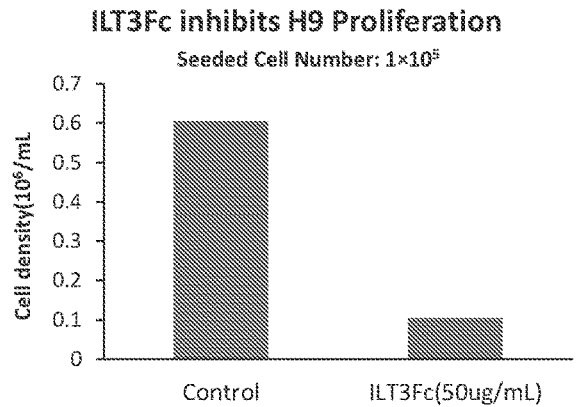
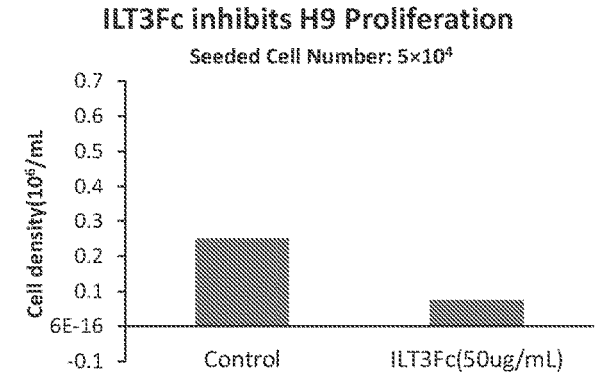
FIG. 6E 40 Hours Post ILT3Fc Treatment
A 3-27-15
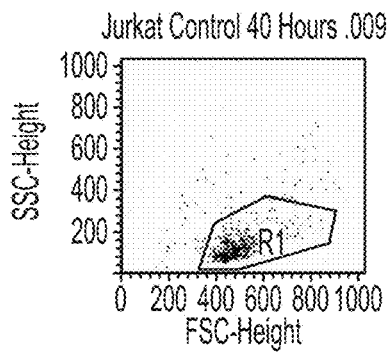
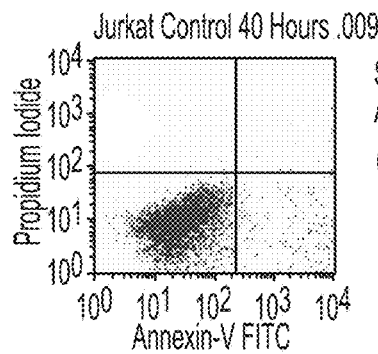
Sample ID: Jurkat Control 40 Hours
Acquisition Date: 27-Mar-15
| Quad | %Gated |
|---|---|
| UL | 0.05 |
| UR | 0.45 |
| LL | 95.53 |
| LR | 3.97 |
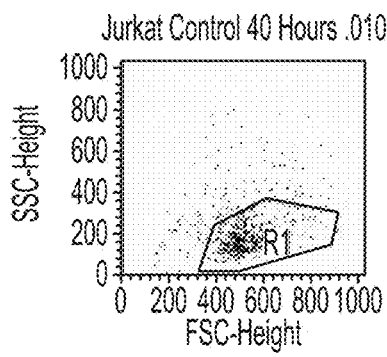
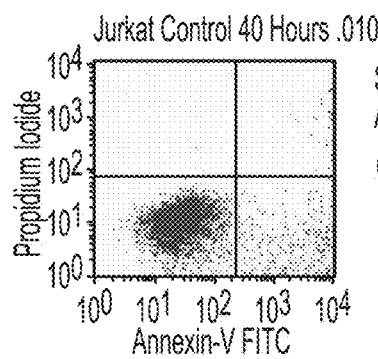
Sample ID: jurkat ilt3fc 40 hours
Acquisition Date: 27-Mar-15
| Quad | %Gated |
|---|---|
| UL | 0.02 |
| UR | 0.71 |
| LL | 90.29 |
| LR | 8.98 |
B
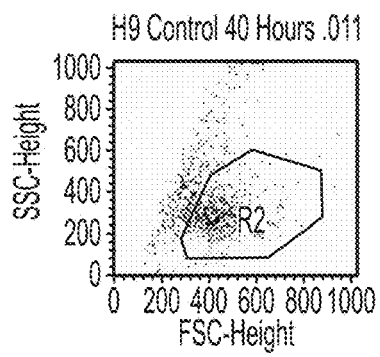
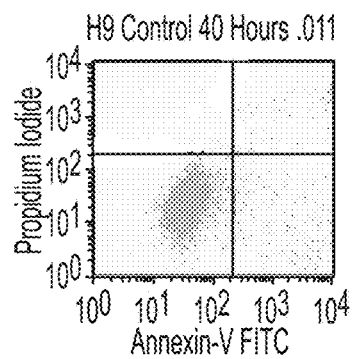
Sample ID: H9 Control 40 Hours
Acquisition Date: 27-Mar-15
| Quad | %Gated |
|---|---|
| UL | 0.12 |
| UR | 1.41 |
| LL | 95.26 |
| LR | 3.21 |
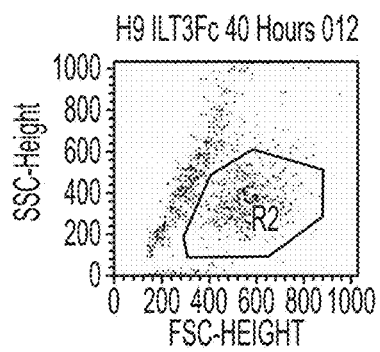
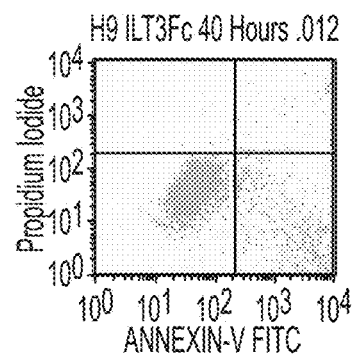
Sample ID: H9 ILT3Fc 40 Hours
Acquisition Date: 27-Mar-15
| Quad | %Gated |
|---|---|
| UL | 0.25 |
| UR | 2.79 |
| LL | 80.22 |
| LR | 16.74 |
FIG. 8

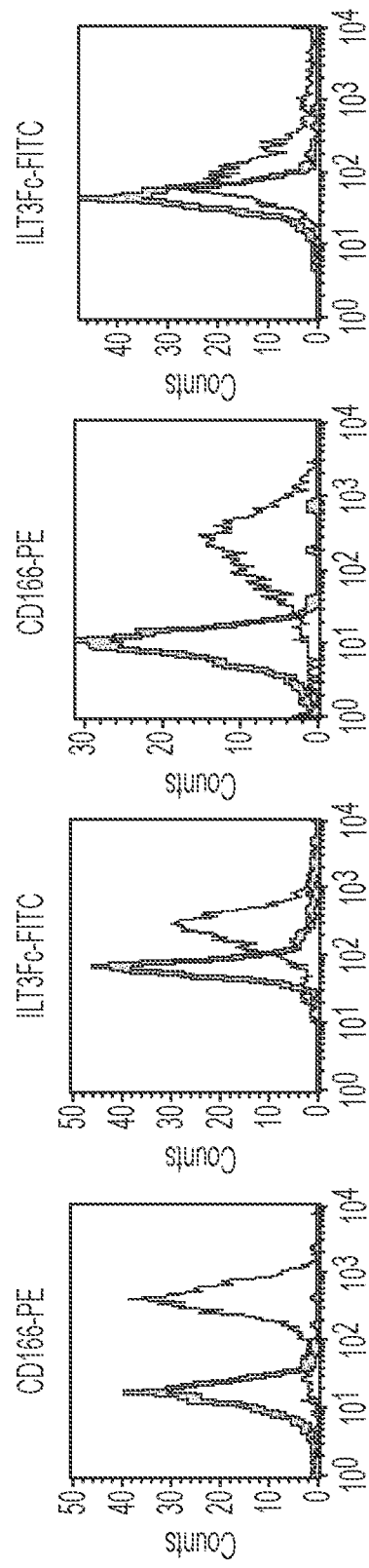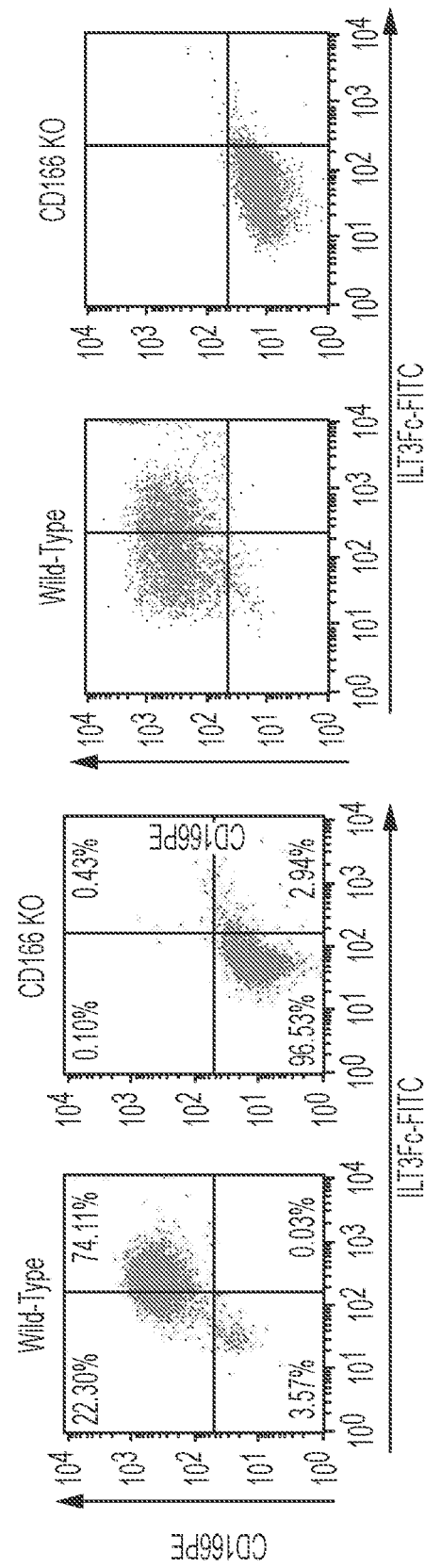
FIG. 9A
FIG. 9B

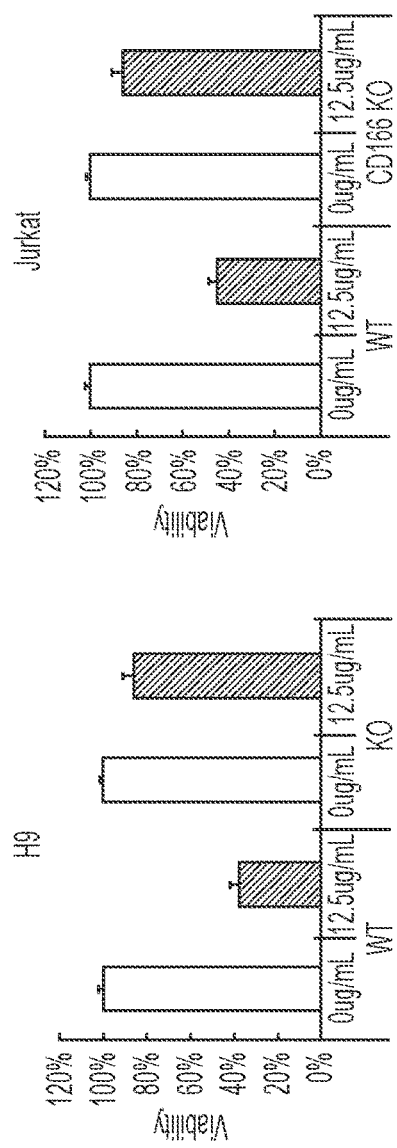
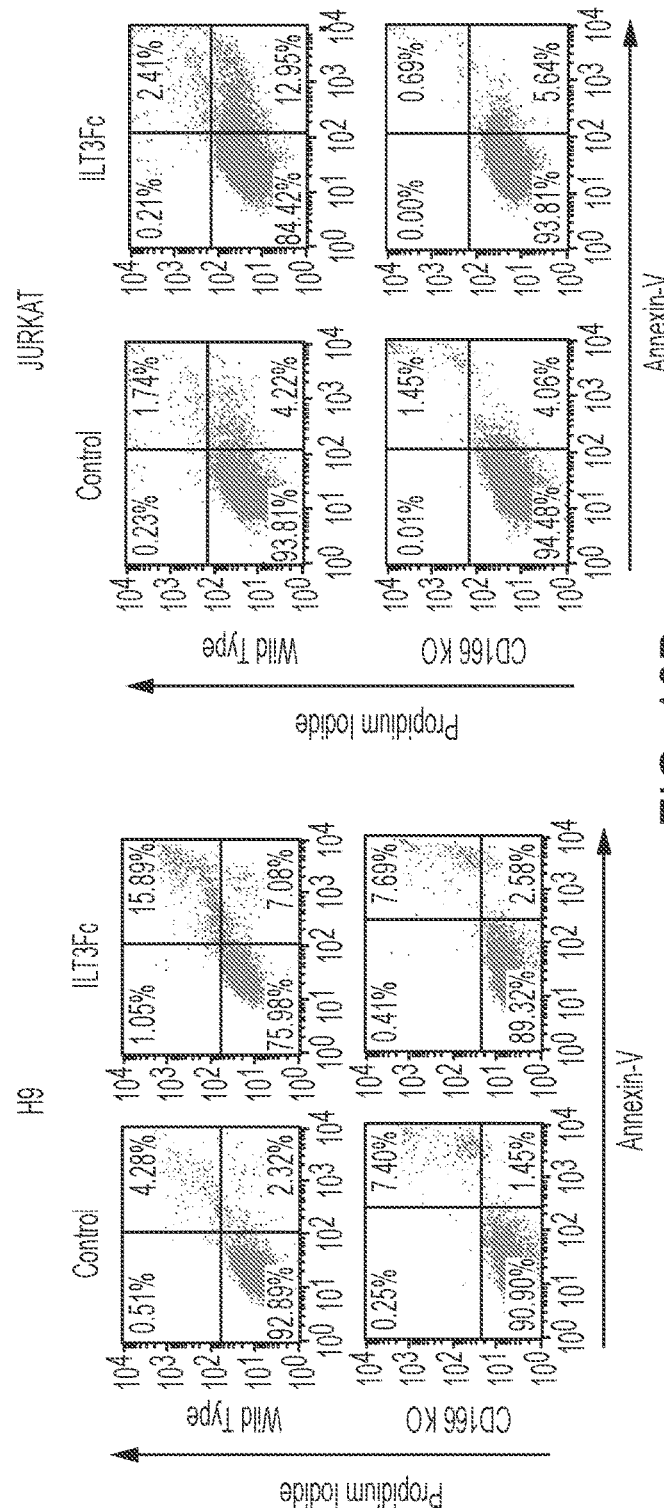
FIG. 10A
FIG. 10B

10,765,742 B2

METHODS OF TREATING CD166-EXPRESSING CANCER

CROSS REFERENCE TO RELATED APPLICATIONS

This application is a 371 national stage application of PCT Application No. PCT/US16/42833, filed Jul. 18, 2016, and claims benefit of Provisional Appln. 62/193,980, filed Jul. 17, 2015, the entire contents of which are hereby incorporated by reference as if fully set forth herein, under 35 U.S.C. § 119(e).

BACKGROUND

In spite of dramatic progress in the treatment of several cancers—such as thyroid cancer, Hodgkin lymphoma, and acute lymphocytic leukemia in children—there has been only limited progress in treating those types of cancer that claim by far the largest toll on human life, including cancer of the breast, prostate, lung, liver, kidney, and colorectal cancers. Therefore there is a great need for an effective cancer therapy with minimal cytotoxic effects.

SUMMARY

It has been discovered that activated lymphocyte cell adhesion molecule (ALCAM)—also known as CD166—is the ligand of the ILT3 receptor. Certain forms of cancer such as leukemia, lymphoma, prostate, breast, lung, kidney, pancreas, and melanoma cancers express the ILT3 ligand CD166 on their surface. It has been further discovered that the binding of ILT3, preferably the recombinant protein, to its ligand CD166 on the surface of CD166-expressing cancer cells, arrested cancer cell growth and initiated apoptosis. Therefore, certain embodiments relate to methods for treating these forms of cancer by administering agents that specifically binds to CD-166, such as ILT3Fc, in therapeutically effective amounts.

These and other features, aspects, and advantages of the present invention will become better understood with regard to the following description, appended claims, and accompanying figures.

BRIEF DESCRIPTION OF THE DRAWINGS

The following drawings form part of the present specification and are included to further demonstrate certain embodiments of the present invention. The invention may be better understood by reference to one or more of these drawings in combination with the detailed description of specific embodiments presented herein.

In FIG. 2A, plots show magnetically sorted CD3+ cells from healthy blood donors were left untreated or triggered by stimulation with Pokeweed Mitogen (PWM) or CD3/CD28 antibodies for 48 hours. Cells were double stained with anti-CD166 PE and ILT3Fc-FITC and analyzed by Flow Cytometry. In FIG. 2B, the table shows that $CD3^+$ T cells were triggered with PWM or CD3/CD28 in the presence or absence of ILT3Fc (50 ug/mL) and stained with either ILT3Fc-FITC or anti-CD166 PE.

In FIG. 3A, plots illustrate Jurkat cells were nucleofected with a CD166 over-expression plasmid and double stained with anti-CD166 APC and ILT3Fc-FITC. In FIG. 3B, plots illustrate for adeno-virus mediated knocking down, H9 cells were infected with CD166 specific shRNA carrying adeno-virus or control virus for 7 days and then double stained with anti-CD166 PE and ILT3Fc-FITC.

FIG. 5A-5B are graphs that illustrate the study of CD166 and ILT3Fc interaction by ELISA. Nunc Maxisorp Plates were pre-coated with increasing concentration (2, 4, 8, 16 ug/ml) of IgG as negative control, CD6-Fc as positive control and ILT3Fc. Binding of recombinant full length CD166 as shown in FIG. 5A and CD166.Fc as shown in FIG. 5B to the bound proteins on the plates was measured by ELISA.

FIG. 6A-6E are graphs that illustrate inhibition of tumor cell growth by ILT3Fc. In FIG. 6A, images of Jurkat cells illustrate clustering after 40 hours of culture with or without ILT3Fc. In FIG. 6B, graphs illustrate CFSE analysis of Jurkat cell growth in the presence or absence of ILT3Fc FIG. 6C are graphs that show CFSE analysis of K562 (left) and SK-MEL-1 (right) cell growth in the presence of various concentrations of ILT3Fc (0 to 50 ug/ml) In FIG. 6D, bar graphs illustrate Trypan blue exclusion analysis of K562 and SK-MEL-1 cell growth in the presence of various concentrations of ILT3Fc (0 to 50 ug/ml) The bar graphs in FIG. 6E illustrate Trypan blue exclusion analysis of Jurkat and H9 tumor cell growth after 72 hours culture with or without ILT3Fc.

FIG. 8A-8B are plots that illustrate Annexin-V/PI analysis of ILT3Fc induced apoptosis in Jurkat (FIG. 8A) and H9 (FIG. 8B) tumor cells after 40 hours in culture.

FIG. 9A-9B FACS analysis of ILT3.Fc binding to cell surface CD166. FIG. 9A: single staining of w/t H9 and w/t Jurkat (light-grey) and CD166-KO-H9 and CD166-KO-Jurkat (dark-grey) with anti-CD166-PE or ILT3.Fc-FITC; FIG. 9B: double staining of the same cells with anti-CD166-PE and ILT3.Fc-FITC. Results were confirmed in 3 independent experiments.

FIG. 10A-B In vitro inhibition of tumor cell proliferation by ILT3.Fc. FIG. 10A: Viable cell counting by trypan blue exclusion of wT/H9 CD166-KO-H9 (left) and of wT/Jurkat and CD166-KO-Jurkat (right) untreated (black bar) or treated for 72 hours (white bar) with ILT3.Fc (12.5 ug/ml). The results were confirmed in 4 independent experiments. FIG. 10B: Annexin-V/PI staining of w/T and CD166-KO H9 (left) and w/T and CD166-KO Jurkat cells (right) grown for 72 hours in medium without (control) or with ILT3.Fc. The results are representative of 3 independent flow cytometry studies.

FIG. 15A: Western blot analysis of phosphorylation of proteins involved in the p70S6K signaling pathway in Jurkat cells. Similar phenomenon was observed in H9 cells. FIG. 15B: Rescue of H9 cells from ILT3.Fc inhibition of cell growth by transfection of constitutively activated p70S6K plasmid (R3A) but not by wild type (WT) or kinase dead (F5A) mutant. Similar data were obtained when Jurkat cells were analysed.

Figure 1:
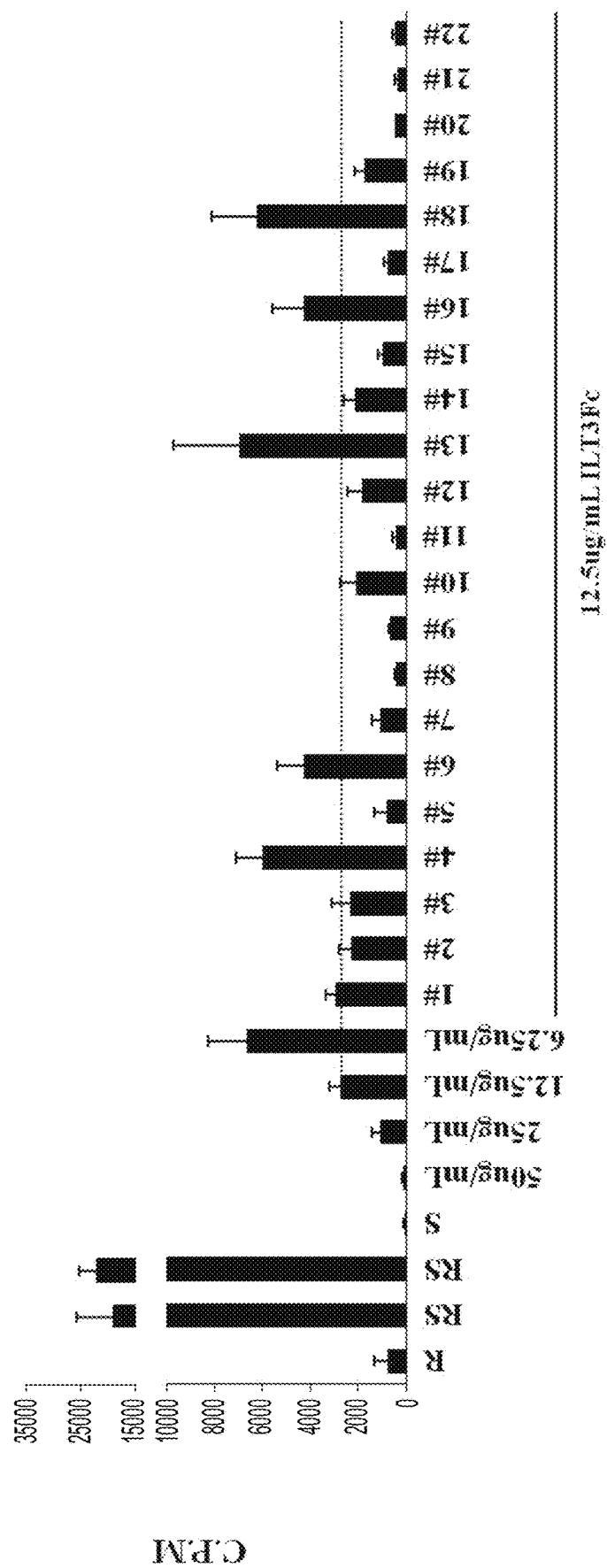
FIG. 1 is a graph showing screening of monoclonal antibodies ("mAbs") for their capacity to attenuate an ILT3Fc induced inhibitory effect on Mixed Leukocytes Reaction ("MLR"). For the MLR assay, responder (R) and stimulator (S) PBMC cells were isolated from healthy blood donors. The stimulator cells ($5\times10^5$ cells/well) were irradiated (3000 Rad) and mixed with R cells ($5\times10^5$ cells/well). Various concentrations of ILT3Fc (from 6.25 ug/mL to 50 ug/mL as indicated) were added to triplicate wells. In parallel rows, constant concentrations of ILT3Fc (12.5 ug/mL) together with different mAbs were added to triplicate MLR. The cultures were incubated for 6 days and labeled with the 3H T during the last 18 hours of the incubation.

In the Summary above, in the Detailed Description and the claims below, as well as in the accompanying figures, reference is made to particular features of the invention. It is to be understood that the disclosure of the invention in this specification includes all possible combinations of such particular features. For example, where a particular feature is disclosed in the context of a particular embodiment or embodiment of the invention, or a particular claim, that feature can also be used, to the extent possible, in combination with and/or in the context of other particular embodiments and embodiments of the invention, and in the invention generally. For the purposes of explanation, numerous specific details are set forth in order to provide a thorough understanding of the present invention. It will be apparent, however, to one skilled in the art that the present invention may be practiced without these specific details.

DETAILED DESCRIPTION

This application is being filed electronically via EFS-Web and includes an electronically submitted sequence listing in .txt format. The .txt file contains a sequence listing entitled "2016-07-18_15003328PC0_ST25" created on Jul. 18, 2016 and is 2,262 bytes in size. The sequence listing contained in this .txt file is part of the specification and is hereby incorporated by reference herein in its entirety.

It has now been discovered that activated lymphocyte cell adhesion molecule (ALCAM)—also known as CD166—is the ligand of the innate immune receptor ILT3 that is expressed by DC and monocytes. Several malignancies (13), including melanoma (32), prostate (33), breast (34), colorectal (35), lung, pancreas (36), hepatocellular (37), leukemia, lymphoma, thymoma and head and neck carcinoma (38) express the ILT3 ligand, now known to be CD166, on their surface. It has been further discovered that the specific binding of ILT3 to its ligand CD166 on the surface of CD166-expressing cancer cells, arrested cancer cell growth and initiated apoptosis. Therefore, certain embodiments relate to methods and compositions for treating CD166-expressing cancers by administering ILT3Fc, full-length ILT3 or any CD166 ligand-binding fragment thereof. Because ILT3Fc is composed of an Ig-like transcript (ILT)3, which is a natural antigen expressed by monocytes, macrophages, and dendritic cells, and an Fc fragment derived from human IgG1, it is less likely to have toxic effects on the body. Without being bound by theory, it is possible that the growth inhibitory effect of ILT3Fc is secondary to its binding to the CD-166 ligand and its subsequent internalization.

The monoclonal antibody 2D9 has also been discovered, which specifically binds to CD166, and therefore can be used to locate and identify CD166-expressing tumors.

In the following description, for the purposes of explanation, numerous specific details are set forth in order to provide a thorough understanding of the present invention. It will be apparent, however, to one skilled in the art that the present invention may be practiced without these specific details. In order that the invention may be readily understood and put into practical effect, particular preferred embodiments will now be described by way of the following non-limiting examples.

1. Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference.

Generally, nomenclatures used in connection with, and techniques of, cell and tissue culture, molecular biology, immunology, microbiology, genetics, protein, and nucleic acid chemistry and hybridization described herein are those well-known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lan, Antibodies: A Laboratory Manual, Cold Spring Harbor Laboratory Press, Cold Spring Harbor, N.Y. (1990); Principles of Neural Science, 4th ed., Eric R. Kandel, James H. Schwart, Thomas M. Jessell editors. McGraw-Hill/Appleton & Lange: New York, N. Y. (2000). Unless defined otherwise, all technical and scientific terms used herein have the same meaning as commonly understood by one of ordinary skill in the art.

The terms "antibody" or "antibodies" as used herein include polyclonal antibodies, monoclonal antibodies (mAbs), chimeric antibodies, CDR-grafted antibodies, anti-idiotypic (anti-Id) antibodies to antibodies that can be labeled in soluble or bound form, as well as fragments, regions or derivatives thereof, provided by known techniques, including, but not limited to enzymatic cleavage, peptide synthesis or recombinant techniques. Included are humanized antibodies.

The term "isolated antibody" as used herein is an antibody that (1) is not associated with naturally-associated components, including other naturally-associated antibodies, that accompany it in its native state, (2) is free of other proteins from the same species, (3) is expressed by a cell from a different species, or (4) does not occur in nature. An "isolated" antibody is one that has been identified, separated and/or recovered from a component of its production environment (e.g., naturally or recombinantly). Preferably, the isolated antibody is free of association with all other components from its production environment, e.g., so that the antibody has been isolated to an FDA-approvable or approved standard. Contaminant components of its production environment, such as that resulting from recombinant transfected cells, are materials that would typically interfere with research, diagnostic or therapeutic uses for the antibody, and may include enzymes, hormones, and other proteinaceous or non-proteinaceous solutes. In preferred embodiments, the antibody will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant cells since at least one component of the antibody's natural environment will not be present. Ordinarily, however, an isolated polypeptide or antibody will be prepared by at least one purification step.

The term "human antibody" as used herein includes all antibodies that have one or more variable and constant regions derived from human immunoglobulin sequences. In a preferred embodiment, all of the variable and constant domains are derived from human immunoglobulin sequences (a fully human antibody). These antibodies may be prepared in a variety of ways, as described below. A humanized antibody is an antibody that is derived from a non-human species, in which certain amino acids in the framework and constant domains of the heavy and light chains have been mutated so as to avoid or abrogate an immune response in humans. Alternatively, a humanized antibody may be produced by fusing the constant domains from a human antibody to the variable domains of a non-human species. Examples of how to make humanized antibodies may be found in U.S. Pat. Nos. 6,054,297, 5,886,152 and 5,877,293, incorporated herein by reference.

An antibody that "specifically binds to" or is "specific for" a particular polypeptide, antigen, or epitope is one that binds to that particular polypeptide, antigen, or epitope with high affinity, i.e. predominantly binding to a particular polypeptide, antigen or epitope over binding to other polypeptides, antigens or epitopes. For example, binding to the CD166 antigen or an epitope thereof is specific when the antibody binds with a $K_D$ of 100 µM or less, 10 µM or less, 1 µM or less, 100 nM or less, e.g., 10 nM or less, 1 nM or less, 500 pM or less, 100 pM or less, or 10 pM or less. The binding affinity ($K_D$) can be determined using standard procedures as will be known by the skilled person, e.g., binding in ELISA and/or affinity determination using surface plasmon resonance (e.g., Biacore™, Proteon™ or KinExA™ solution phase affinity measurement which can detect down to fM affinities (Sapidyne Instruments, Idaho)). Antibody fragments that have specific binding affinity for CD166 can be generated by known techniques. Such antibody fragments include, but are not limited to, $F(ab')_2$ fragments that can be produced by pepsin digestion of an antibody molecule, and Fab fragments that can be generated by reducing the disulfide bridges of $F(ab')_2$ fragments. Alternatively, Fab expression libraries can be constructed. See, for example, Huse et al. (1989) Science 246:1275-1281. Single chain Fv antibody fragments are formed by linking the heavy and light chain fragments of the Fv region via an amino acid bridge (e.g., 15 to 18 amino acids), resulting in a single chain polypeptide. Single chain Fv antibody fragments can be produced through standard techniques, such as those disclosed in U.S. Pat. No. 4,946,778.

The terms "selectively binds" and "specifically binds" are used interchangeably herein to mean the specific or preferential affinity with which two or more proteins interact such as an antibody with an antigen, or a protein with a substrate. For example, ILT3Fc specifically binds to CD166. "Specific binding" of an active agent, such as the ILT3 and ILT3Fc means that the agent binds to the target protein, such as ILT3 ligand/CD166, with greater affinity than it binds to unrelated antigens.

The term "administering" as used herein, means a manner which is affected or performed using any of the various methods and delivery systems known to those skilled in the art. Administering can be performed, for example, topically, intravenously, pericardially, orally, via implant, transmucosally, transdermally, intramuscularly, subcutaneously, intraperitoneally, intrathecally, intralymphatically, intralesionally, or epidurally. Administering can also be performed, for example, once, a plurality of times, and/or over one or more extended periods.

The terms "active agents" and "therapeutic agents" are used interchangeably to mean ILT3Fc which binds to CD166, as well as full-length ILT3, or any CD166-ligand-binding fragment thereof including the water-soluble extracellular domain of ILT3 that significantly reduces or arrests the growth of a CD166-expressing cancer, or causes apoptosis of the cancer cells. In some embodiments full-length ILT3 and ILT3 fragments are conjugated to one or more Fc fragments. Active agents of the invention specifically bind to CD166.

The term "biological sample" as used herein, means a variety of sample types obtained from an organism and can be used in the embodiments described. The sample is selected from any part of a person's body, including, but not limited to, blood, lymph nodes, spleen, or bone marrow aspirates. Preferred samples for diagnosing cancers that express the ILT3 ligand CD166 include blood (including plasma and serum), bone marrow aspirates, fine needle aspirates, body fluids (such as pleural fluid, cerebra-spinal fluid). The term encompasses samples that have been manipulated in any way after their procurement, such as by treatment with reagents, solubilisation, or enrichment for certain components. The term encompasses a clinical sample.

The term "CD166" as used herein, is synonymous with "the ILT3 ligand" and it means a 100-105 kD type I transmembrane glycoprotein that is a member of the immunoglobulin superfamily of proteins. In humans, it is encoded by the ALCAM gene. It is also called MEMD, SC-1/DM-GRASP/BEN in the chicken, and KG-CAM in the rat. Some literature sources have also cited it as the CD6 ligand (CD6L). It is expressed on activated T cells, activated monocytes, epithelial cells, fibroblasts, neurons, melanoma cells, and also in sweat and sebaceous glands. CD166 protein expression is reported to be upregulated in a cell line deriving from a metastasizing melanoma. Information of the protein and mRNA sequences are included in the Table 4. CD166, or ILT3 ligand, is expressed transiently on the surface of up to about 10-30% of normal T cells from peripheral blood monocytes (PBMC) which have been allo-activated by exposure to HLA mismatched cells. The ligand-binding site on ILT3 is in the extracellular domain of ILT3. In the context of cancer treatment as taught herein.

The terms "ILT3 ligand" and "CD166" are used interchangeably herein to mean the molecule expressed on the surface of activated T-cells and certain cancer cells such as leukemia (i.e. T-ALL cells), prostate, breast, lung, kidney, pancreas, and melanoma cells to which ILT3Fc and certain fragments thereof specifically bind.

The term "ILT3" as used herein means "Immunoglobulin-Like Transcript-3", and is synonymous with "ILT-3", "LIR-5", "CD85K" and "LILRB4." The mRNA coding sequence for human ILT3 is provided under GenBank No. U82979. Human ILT3 is a transmembrane protein having 447 amino acids with a predicted molecular mass of about 47 kD. ILT3 behaves as an inhibitory receptor when cross-linked to a stimulatory receptor. ILT3 has an extracellular region that includes N-terminal amino acids 1-259 and a signal peptide of amino acids 1-16; a transmembrane domain that includes amino acids 260-280; and a cytoplasmic domain that includes amino acids 281-448. ILT3 has cytoplasmic domain which includes an ITIM motif at amino acids 412-415 and 442-445. The extracellular domain of contains two Ig domains. "ILT3" shall mean the gene, mRNA, or protein of "Immunoglobulin-Like Transcript-3", and is synonymous with "ILT-3", "LIR-5", "CD85K" and "LILRB4". The mRNA coding sequence for human ILT3 is provided under GenBank No. U82979.

The term "ILT3Fc" as used herein, means a water-soluble recombinant protein having the extracellular domain of human ILT3 (ECD) operably affixed to the Fc portion of an immunoglobulin. In an embodiment, the Fc portion comprises a function-enhancing mutation, such as a mutation that inhibits the binding of the Fc portion of an immunoglobulin to an Fc receptor. In an embodiment the Fc portion is derived from human IgG 1. In one example, the function-enhancing mutation in the Fc portion of the immunoglobulin is an Asn→Gln point mutation at amino acid residue 77 of the Fc portion of human IgG1. The Fc portion of ILT3Fc may be substituted with any other peptide that promotes dimerization or oligomerization of the probe or otherwise stabilizes the probe. For example, the peptide may comprise cysteine residues that form disulfide bonds or other residues that promote covalent or noncovalent interactions between the peptides such that the peptides mediate dimerization or oligomerization. Exemplary oligomerization domains are described in, e.g., WO 00/69907, WO 99/62953, WO 98/56906, WO 98/18943, and WO 96/37621.

The term "detectable probe" as used herein means a probe for use in the kits described herein to detect, inter alia, CD166 expression on certain cancer cell surfaces. The probes may be detected or visualized using well known methods such as radioactive isotopes such as $^{125}I$, $^{32}P$, $^{35}S$, and $^3H$, enzymes, chemiluminescent agents, and fluorescent dyes. Fluorescent tracers for use in the embodiments include GFP and derivatives, Diamidino yellow, Fast blue, Horseradish peroxidase, Cholera toxin B, Pseudorabies virus, Hydroxystilbamidine, Texas Red, and Fluorescein isothiocyanate, and any others known in the art. Green fluorescent protein (GFP) was used in the experiments described herein, however there are now many different mutants of GFP [Shaner N, Steinbach P, Tsien R (2005). "A guide to choosing fluorescent proteins" (PDF). *Nat Methods* 2 (12): 905-9.] A list of various fluorescent proteins can be found on the World Wide Web at domain nic.ucsf of domain category edu in folder dokuwiki in file doku.php?id=fluorescent_proteins. Different types of chemical labels or tags can be conjugated to secondary or primary antibodies against ILT3 or ILT3Fc to facilitate their visualization (i.e., detection and measurement.) The choice of label or tag depends on the sensitivity required, ease of conjugation with the probe, stability requirements, and available instrumentation.

The terms, "extracellular domain of ILT3" or "ECD" or "ED" as used herein, mean the N-terminal 258 amino acid residues of ILT3 (e.g., human ILT3 having the sequence of GenBank Accession No. U82979). The extracellular domain of contains two Ig domains, one or both of which are likely to contribute to the ILT3 ligand binding. The extracellular domain of ILT3 includes, for example, the IgG 1-like domain 1 (residues 42-102 of human ILT3), the IgG 1-like domain 2 (residues 137-197 of human ILT3), and the N-terminal 250, 240, 230, 220, 210, 200, 190, 180, 170, 160 or 150 amino acid residues of ILT3.

The term "function-enhancing mutation", as used herein, means any mutation which confers a physical property (e.g., reduced binding of the Fc moiety to an Fc receptor) to the polypeptide which permits it to better accomplish its therapeutic role (e.g., through increasing its half-life or reducing adverse effects otherwise caused by a subject's immune system).

The terms "ILT3 ligand-binding probe" and "CD166-binding probe" are used interchangeably herein to mean a molecule that specifically binds to ILT3 ligand, CD166 that has now been discovered to be located on the surface of certain cancers. The ILT3 ligand-binding probes include the recombinant protein (ILT3Fc), fragments of ILT3Fc or full-length ILT3, or CD166-binding fragments of ILT3, and anti-CD166 antibodies and fragments thereof. The probes can be used alone or they can be bound to a compound that stabilizes the probe or increases binding of the probe to the targeted ILT3 ligand such as Fc. Since there is a high level of sequence homology among various species, the ILT3 ligand-binding probes, though preferably including or derived from human ILT3, can come from any species as long as it specifically binds to ILT3 ligand on a targeted cancer cell or T-cell.

The terms "immunoglobulin" and "antibody" are used synonymously herein, and are used in association with any anti-CD166 antibody that has high affinity. For diagnostic use, the anti-CD166 antibodies specifically bind to CD166 expressed on the surface of a cancer cell. Included, by way of example, are both naturally occurring and non-naturally occurring antibodies, polyclonal and monoclonal antibodies, any antigen-binding fragments (e.g., Fab fragments, as opposed to Fc fragments) thereof, chimeric antibodies (e.g., humanized antibodies) and wholly synthetic antibodies, and antigen-binding fragments thereof. Within the scope of the term "antibody" are antibodies that have been modified in sequence, but remain capable of specifically binding to CD166. Examples of modified antibodies include interspecies chimeric and humanized antibodies; antibody fusions; and heteromeric antibody complexes, such as diabodies (bispecific antibodies), single-chain diabodies, and intrabodies (see, e.g., Marasco (ed.), Intracellular Antibodies: Research and Disease Applications, Springer-Verlag New York, Inc. (1998) (ISBN: 3540641513), the disclosure of which is incorporated herein by reference in its entirety).

The terms "individual," "subject" and "patient," as used herein, are used interchangeably and mean any human subject for whom diagnosis, treatment, or therapy is desired.

The terms "polypeptide" and "protein" are used interchangeably herein, and each means a polymer of amino acid residues. The amino acid residues can be naturally occurring or chemical analogues thereof. Polypeptides and proteins can also include modifications such as glycosylation, lipid attachment, sulfation, hydroxylation, and ADP-ribosylation.

The terms "significantly lower" and "significantly reduced" mean a statistically significant reduction or lowering, such as reducing CD166-expressing cancer by a statistically significant amount, for example a statistically significant post-treatment reduction in tumor growth, tumor volume, or the number of circulating cancer cells (e.g., in the case of leukemias) compared to pretreatment levels.

The terms "significantly increasing" or "significantly higher" as used herein mean a statistically significant increase, e.g., a statistically significant increase in the apoptosis of CD166-expressing cancer post-treatment with an active agent such as ILT3Fc compared to a pretreatment level of apoptosis. The term "significantly higher" as used herein with respect to the level of detectably labeled cancer cells means about one standard deviation above the mean of a normal population, which may vary depending on the sample size of the normal and cancer populations and the type of cancer.

The term "therapeutically effective amount" as used herein means of an active agent or pharmaceutical composition in an amount that achieves the intended therapeutic effect, e.g., alleviation, amelioration, palliation or elimination of one or more manifestations of the disease or condition in the subject. The full therapeutic effect does not necessarily occur by administration of one dose and may occur only after administration of a series of doses. Thus, a therapeutically effective amount may be administered in one or more administrations.

The term "treating" as used herein, means slowing, stopping or reversing the effects of a disease, particularly cancer. As used herein, the terms "treatment," "treating," and the like, as used herein refer to obtaining a desired pharmacologic and/or physiologic effect. The effect may be prophylactic in terms of completely or partially preventing a condition or disease or symptom thereof and/or may be therapeutic in terms of a partial or complete cure for a condition or disease and/or adverse effect attributable to the condition or disease. "Treatment," includes any treatment of a condition or disease in a mammal, particularly in a human, and includes: (a) preventing the condition or disease or symptom thereof from occurring in a subject which may be predisposed to the condition or disease but has not yet been diagnosed as having it; (b) inhibiting the condition or disease or symptom thereof, such as, arresting its development; and (c) relieving, alleviating or ameliorating the condition or disease or symptom thereof, such as, for example, causing regression of the condition or disease or symptom thereof.

2. Overview

A. ILT3

The induction of antigen-specific regulatory T cells ($T_{reg}$) from primed lymphocytes is a complex process that limits the "collateral damage" resulting from protective immunity and inflammatory responses against self- and non-self-antigens. There is ample evidence that dendritic cells (DC) can prevent and inhibit T cell-mediated effector responses acquiring tolerogenic property and inducing anergy or instructing T cells to become suppressor/regulatory cells (1).

The human Ig-like transcript 3 (ILT3), also known as LIRB4/LIR5/CD85k, belongs to a family of innate immune receptors that are expressed by DC and monocytes (2). This ILT receptor displays a long cytoplasmic tail containing ITIMs, which mediate inhibition of cell activation by recruiting tyrosine phosphatase SHP-1 (2). Upregulation of ILT3 on the membrane of DC can be induced in a cytokine-independent manner by direct interaction with human CD8+T suppressor cells (Ts), generated by repeated allostimulation in MLC, or alternatively by exposure to some cytokines such as IL-10, IFN-α, IFN-β (3-5), or other agents, such as vitamin D receptor agonists (6, 7). Upregulation of ILT3 expression or ILT3 transfection of DC results in inhibition of CD40 signaling and of NF-κB activation (3). Tolerogenic human DC is characterized by a high expression of ILT3 on their membrane and by their capacity to induce anergy and the differentiation of Treg/Ts (3, 4). In contrast, knockdown (KD) of ILT3 from DC (ILT3 KD-DC) increases their TLR responsiveness, as reflected in synthesis and secretion of proinflammatory cytokines (IL-1α and β, IL-6, and type I IFN) and migration factors CXCL10 and CXCL11. ILT3KD-DC enhance T cell proliferation and secretion of IFN-γ and IL-17 when pulsed with CMV or used as allostimulators in MLC (8).

These data, in conjunction with the finding that CD8+ T cells from rejection-free heart, kidney, or liver transplant recipients induced the upregulation of ILT3 in donor APC, substantiate the importance of these inhibitory receptors for maintenance of immunologic quiescence (1).

The extracellular domain of ILT3 retains the T cell inhibitory function even upon deletion of the cytoplasmic, ITIM-containing tail, because DC transfected with a construct made up of only the extracellular portion were still capable to elicit the differentiation of CD8+Ts (9). On the basis of this finding, soluble ILT2 was engineered form a soluble form of ILT3, which was expressed as an ILT3Fc fusion protein and tested its immunomodulatory activity. This recombinant protein inhibited primary and secondary T cell responses in MLC and blocked the differentiation of CD8+ cytotoxic T cells (CTL). Furthermore, it elicited the in vitro and in vivo differentiation of CD8+Ts, which produced no cytokines, inhibited T cell reactivity and induced the upregulation of ILT3 on priming APC (9-11). In vivo studies showed that ILT3Fc induced tolerance to allogeneic human pancreatic islet cells transplanted in humanized diabetic NOD/SCID mice (10, 11).

B. ALCAM/CD166

Adhesion molecules are divided into broad categories, which include immunoglobulins, cadherins, selectins, integrins, and mucins. Adhesion molecules can be involved in tumor cell—tumor cell adhesion, tumor cell—endothelial cell adhesion, or tumor cell—matrix adhesion. These adhesions are essential at different times during primary tumor formation or metastasis. Adhesion molecules can be upregulated or downregulated during the process, as is the case of ALCAM/CD166, a member of the immunoglobulin superfamily (13).

ALCAM is a glycoprotein that is involved in both homotypic or homophilic and heterotypic or heterophilic interactions (14). ALCAM has 5 extracellular immunoglobulin domains (2 NH2-terminal, membrane-distal variable-(V)-type (V1, V2 or D1, D2) and 3 membrane-proximal constant-(C2)-type Ig folds) [C1, C2, C3], a transmembrane region, and a short cytoplasmic tail. (14, 15). The N-terminal domain (D1) is exclusively involved in ligand binding, whereas membrane proximal domains (C2, C3 or D4, D5) are required for homophilic interactions. The cytoplasmic tail contains 32 amino acid residues (13-20).

Until now, the only known ligand of CD166 has been CD6, a surface receptor expressed by T lymphocytes and thymocytes as well as by a subset of B cells. Its extracellular region contains 3 scavenger receptor cysteine-rich (SRCR) domains, indicating that CD6 is a member of the SRCR superfamily.

The role of ALCAM in T-cell biology has been widely studied (15, 21-31). It has been reported that long-term engagement of the dendritic cell ALCAM and CD6 expressed on T-lymphocytes was essential for proliferation of T cells long after the initial contact with APC had been established (31). This finding is consistent with image analysis of T-cell antigen-presenting cell conjugates, which demonstrates that CD6 and ALCAM co-localize with the T-cell receptor complex at the center of the immunological synapse (24), and it extends findings (25) that the ALCAM-CD6 interaction is required for optimal activation of T cells.

ALCAM expression has been found in several malignancies (13), which include melanoma (32), prostate (33), breast (34), colorectal (35), lung, pancreas (36), hepatocellular (37), and head and neck carcinoma (38).

In spite of the importance of CD166 in T cell immunobiology, its potential importance in tumors of hematopoietic origin has not been evaluated before. Of notice, numerous investigations indicate that CD166 might be a common denominator of progenitor cells in many malignancies.

3. Summary of Experimental Results

Figure 6A:
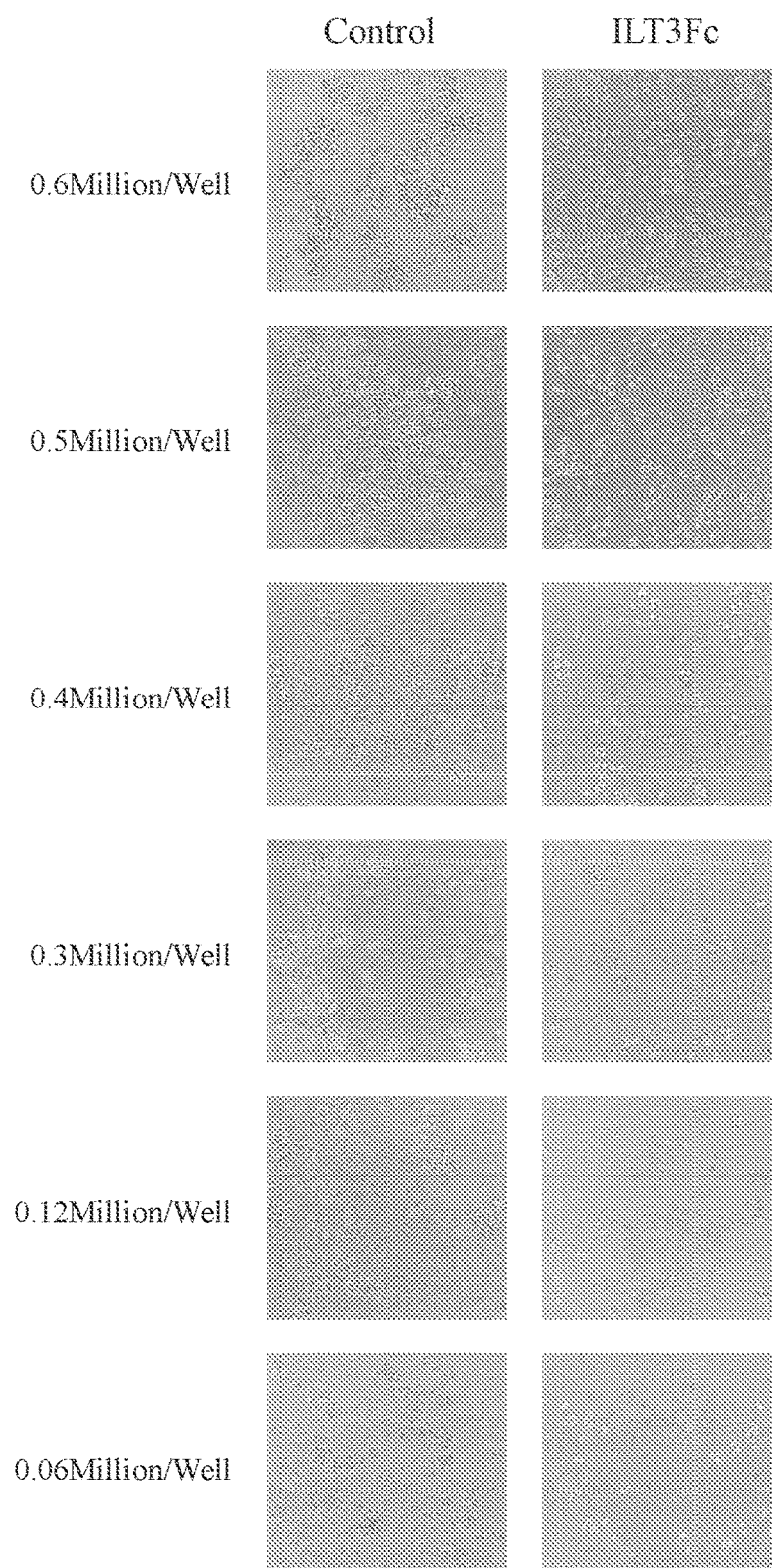
Figure 6B:
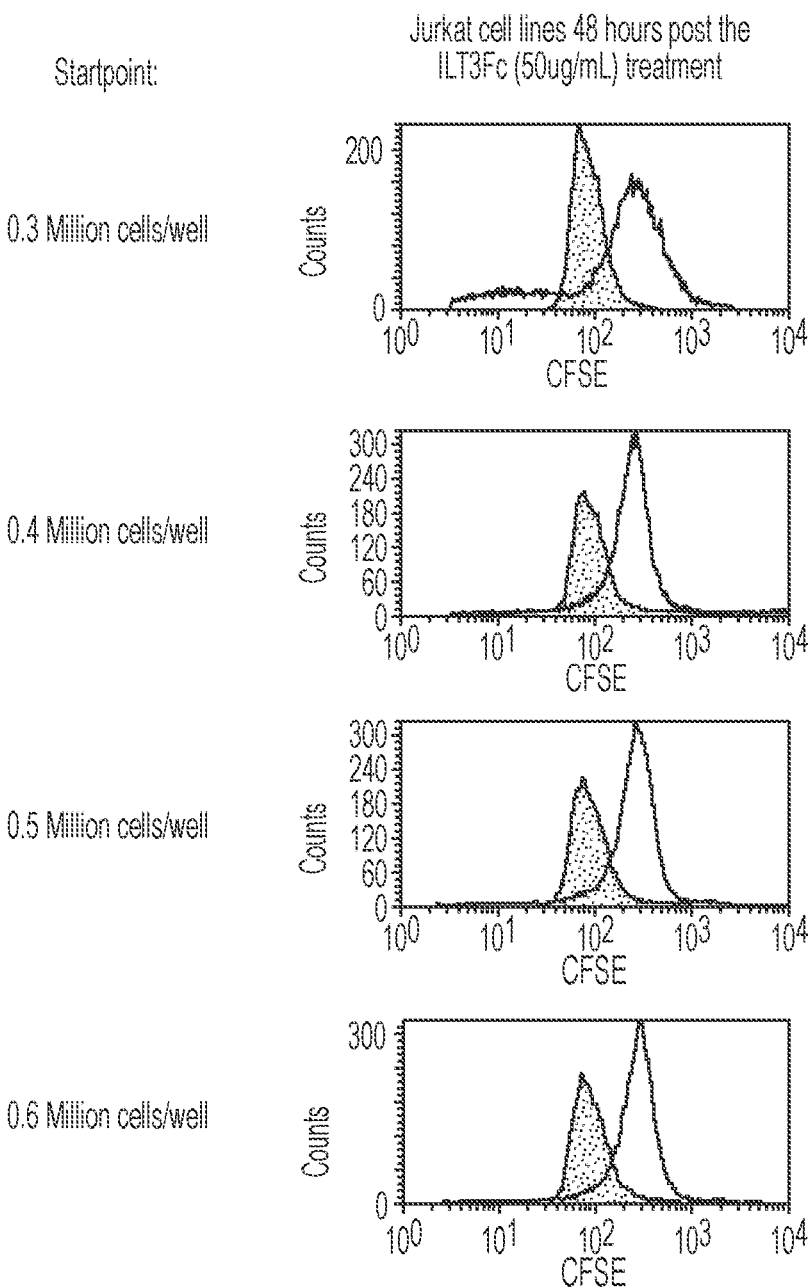
Figure 6D:
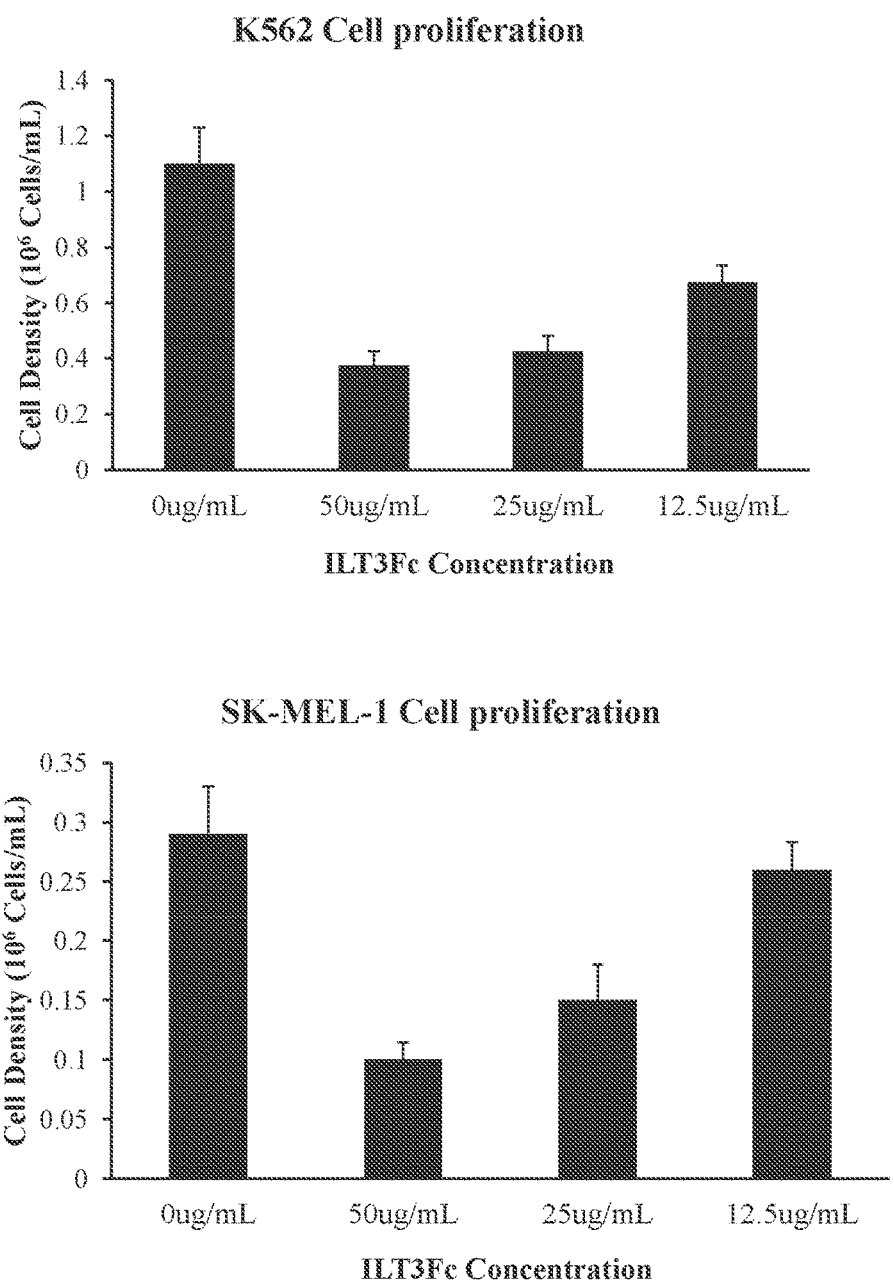
Figure 7:
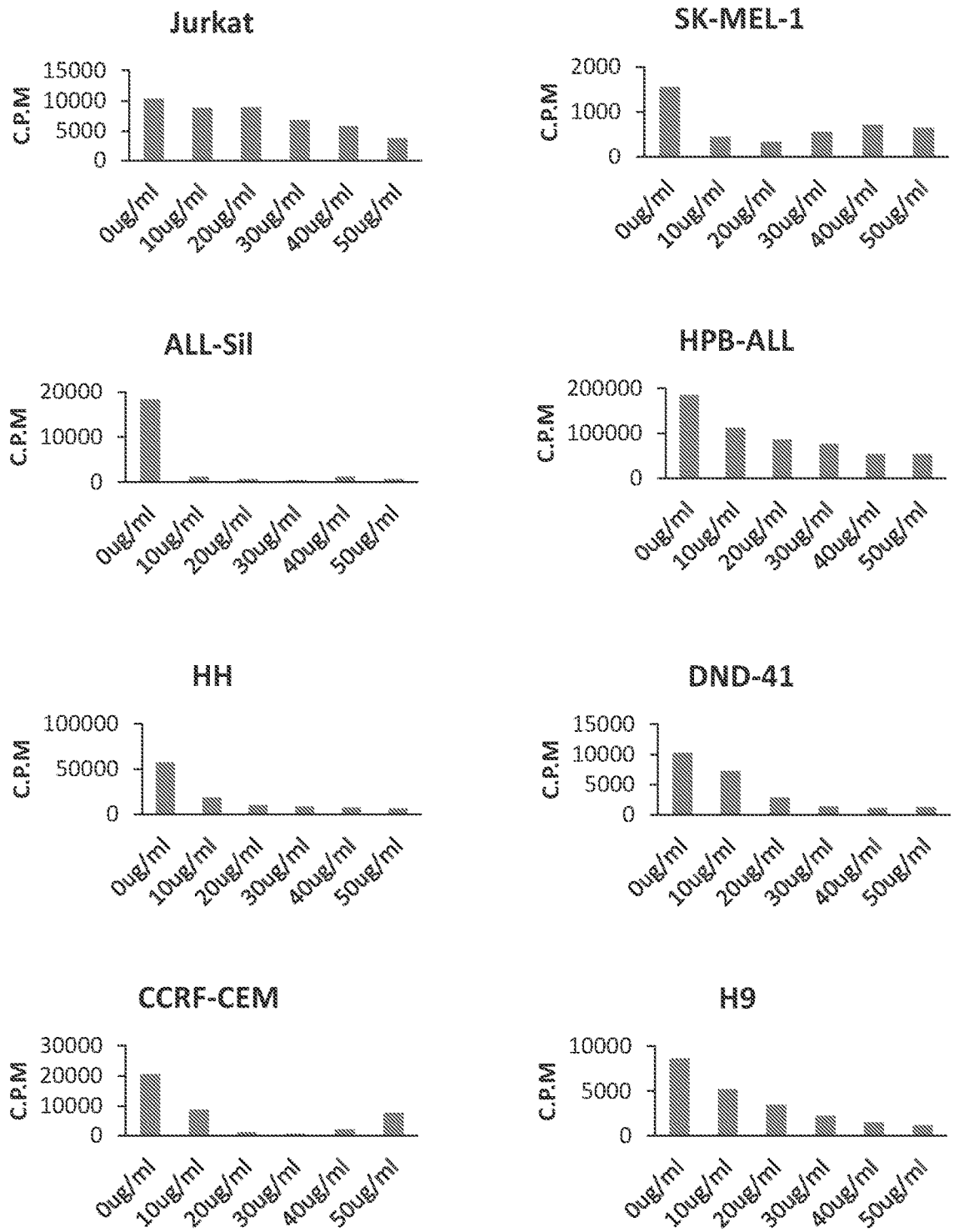
FIG. 7 includes bar graphs that illustrate the effect of various concentrations of ILT3Fc on the proliferation of tumor cell growth as measured by 3H-TdR incorporation at 96 hours.

1. ILT3Fc binds to CD166-positive populations of activated T cells.
2. ILT3Fc binding decreased from 46% in control virus-infected H9 cells to less than 20% in cells where CD166 was knocked down ("CD166 KD cells") using adeno-virus carrying CD166-specific short hair RNA.
3. Flow cytometry showed that ILT3Fc binding increased significantly with CD166 over-expression showing that CD166 expression was positively correlated with the ILT3Fc binding to H9 tumor cells.
4. Some known CD166 involved protein-protein interaction partially block the ILT3Fc binding.
5. Both full length CD166 and CD166-Fc bind to ILT3Fc in a dose-dependent manner, showing that CD166 is the ligand of ILT3.
6. ILT3Fc binding is associated with CD166 expression on tumor cell lines and binding of ILT3Fc is primarily to the D domain of CD166 in most T-ALL cells and in the SK-MEL-1 melanoma cell line.
7. ILT3Fc strongly inhibited (by 50 to 90%) the growth of all tumor cell lines tested including T-ALL and other tumor cell lines derived from melanoma (SK-MEL-1) or chronic myelogenous leukemia (K562)) (FIGS. 6 A, B, C, D, E and FIG. 7).
8. ILT3Fc administration reduced tumor burden and tumor volume in NSG mice transplanted with T cell lymphoma H9cells and increased survival rates in such mice.
9. ILT3Fc treatment of mediates cancer cell inhibitory effects via the p70S6K signaling pathway.

4. Embodiments

In order to identify the ligand of ILT3Fc, a mAb-based strategy was developed wherein mice were immunized with H9, which is a cutaneous T cell lymphoma cell line, and hybridoma supernatants were screened for monoclonal antibodies that bind with high affinity to T-cell Acute Lymphoblastic Leukemia (T-ALL) cell lines which are known to bind ILT3Fc-FITC, and as a control, to resting CD3 T cells known not to bind ILT3Fc. As shown in Table 1, one of these antibodies, 2D9 (anti-CD166), showed the same pattern of binding as ILT3Fc. Other monoclonal antibodies from the screened hybridoma supernatants were purified and used for immuno-precipitation of the antigen they recognized the cell surface of H9, the immunizing cell line. As shown in Table 2, the resulting bands were mass-spectrometry analyzed and shown to recognize IMPDH2 (2E4), ERP5 (1A5) and CD71 (2C1, 2C10 and 106).

ILT3Fc was shown to bind to its newly discovered ligand CD166 on certain tumor cell lines, including most T-ALL cells and SK-MEL-1 melanoma cell lines, thereby dramatically reducing tumor cell growth and inducing apoptosis. Based on the results described here, certain embodiments of the invention are directed to methods of treating subjects having CD166-expressing cancers by administering therapeutically effective amounts of an active agent as described herein, preferably ILT3Fc, that binds to CD166 on the surface of cancer cells thereby treating the cancer, for example by arresting the growth of the cancer cells and/or inducing apoptosis, thereby treating the CD166-expressing cancer. Any CD166-expressing cancer can be treated with ILT3Fc or other herein-described active agent. ILT3Fc has low toxicity of ILT3Fc because it is composed of Ig-like transcript (ILT)3, a natural antigen expressed by monocytes, macrophages, and dendritic cells, and an Fc fragment derived from human IgG1. Thus, relatively high doses can be administered even systemically. Local administration of an active agent such LT3-Fc directly to the tumor or immediate area surround the tumor permits even higher doses and is a further embodiment of the invention.

Another embodiment is directed to the newly discovered anti-CD166 monoclonal antibody 2D9 that specifically binds to CD166, and therefore can be used to locate and identify CD166-expressing tumors. Anti-CD166 antibodies could also be used to deliver cytotoxic agents to CD166-expressing cancer cells. Yet other embodiments are directed to kits comprising anti-CD166 antibodies including 2D9, and an agent that binds to the antibody which agent can be visualized, preferably visually, to detect the presence of CD166-expressing cancers.

A further embodiment pertains to a method of determining if a subject afflicted with cancer has a CD166-expressing cancer that would be susceptible to treatment methods taught herein. In a specific example, the embodiment pertains to a method that involves obtaining a biological sample from a subject afflicted with cancer, wherein the biological sample comprises cancer cells; contacting the cancer cells in the biological sample with an anti-CD166 antibody or a CD166-binding fragment thereof; determining whether the cancer cells bind to the anti-CD166 antibody, or CD166-binding fragment thereof; and if the cancer cells bind to the anti-CD166 antibody, or CD166-binding fragment thereof, then treating the cancer by administering to the subject a therapeutically effective amount of an agent selected from the group consisting of ILT3, or a CD166-binding fragment thereof, and ILT3Fc, or a CD166-binding fragment thereof. Specific examples of biological samples to be tested include blood or component thereof, bone marrow or a tumor sample. In an even more specific example, the anti-CD166 antibody includes the monoclonal 2D9 antibody, or a CD166-binding fragment thereof. Examples of cancers that are tested include leukemia, lymphoma, prostate, breast, lung, kidney, pancreas, and melanoma cancers. Leukemia includes chronic myelogenous leukemia (AML), Acute B cell leukemia line or adult T-cell leukemia (T-ALL), and the lymphoma is cutaneous T cell lymphoma.

A. Routes of Dosage and Administration

Determining an effective amount of an active agent such as ILT3Fc or of pharmaceutical compositions comprising them for use in the instant invention can be done based on animal data using routine computational methods. A therapeutically efficient dose and regimen for treatment of CD166-expressing cancers is within the skill of the art taking into consideration, for example, the condition and weight of the patient, the extent of desired treatment and the tolerance of the patient for the treatment. The actual amount administered, and rate and time-course of administration, will depend on the nature and severity of what is being treated. It will also depend upon toxicity of the therapeutic agent, as determined by pre-clinical and clinical trials. Prescription of treatment, e.g., decisions on dosage etc., is within the responsibility of general practitioners and other medical doctors.

Determining an effective amount of the active agents for use in embodiments of the instant invention can be done based on animal data using routine computational methods. In general, dosage is from 0.001 μg to 100 g and may be administered once or several times daily, weekly, monthly, or yearly. In one embodiment, the effective amount, administered intravenously, is between about 0.5 mg/kg and about 100 mg/kg of polypeptide. In another embodiment, the effective amount, administered intravenously, is between about 1 mg/kg and about 20 mg/kg of polypeptide, or from about 3, 5 or 10 mg/kg of polypeptide. In an embodiment, the effective amount is administered locally to the tumor or area around the tumor for example by injection or via an implantable pump. In various embodiments of the instant methods, ILT3Fc or other active agent is administered in a single dose, or in multiple doses on the same day or on different days. The duration of treatment depends on the response of the cancer.

Dosing is dependent on severity and responsiveness of the condition to be treated, with course of treatment lasting from several days to several months or until a reduction or a diminution of the disease state is achieved. Optimal dosing, dosing methodologies and repetition rates can be determined by monitoring the growth of the CD166-expressing cancer using methods known in the art including x-rays, CAT scans, PET scans, MRI, etc. and from the patient's general reaction to the drug including any adverse side effects which vary from patient to patient. Therapeutically effective amounts may vary depending on the relative potency of individual compositions, and can generally be routinely calculated based on molecular weight and EC50s in in vitro and/or animal studies. For example, given the molecular weight of drug compound and an experimentally derived effective dose such as an $IC_{50}$, for example, a dose in mg/kg is routinely calculated.

Administration of an active agent, including ILT3Fc or pharmaceutical compositions comprising them, including isolated and purified forms, may be accomplished using any of the conventionally accepted modes of administration of agents which are used to treat cancer. Pharmaceutical compositions of the present invention may be administered in a number of ways depending upon whether local or systemic treatment is desired and upon the area to be treated. Administration may be oral, parenteral, or topical (including ophthalmic, vaginal, rectal, intranasal, epidermal and transdermal). Parenteral administration includes intravenous drip, subcutaneous, intraperitoneal or intramuscular injection, pulmonary administration, e.g., by inhalation or insufflation, or intracranial, e.g., intrathecal or intraventricular administration.

B. Antibodies

1. Antibody Definitions

The term "antibody" herein is used in the broadest sense and specifically covers monoclonal antibodies, (e.g., the anti-CD166 antibody 2D9), polyclonal antibodies, multispecific antibodies (e.g., bispecific antibodies) formed from at least two intact antibodies, and antibody fragments or variants so long as they exhibit the desired biological activity against CD166. The anti-CD166 antibody can be a polyclonal or a monoclonal antibody. The anti-CD166 antibody is preferably a humanized antibody. In one embodiment of the methods described herein, the anti-CD166 otherwise known as antibody (2 D9) is a fully human antibody, mono- or polyclonal.

The term "antibody" herein is used in the broadest sense and specifically covers monoclonal antibodies, polyclonal antibodies, multispecific antibodies (e.g., bispecific antibodies) formed from at least two intact antibodies, and antibody fragments so long as they exhibit the desired biological activity.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites and have their usual meaning which is well-known in the art.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively. The subunit structures and three-dimensional configurations of different classes of immunoglobulins are well known and described generally in, for example, Abbas et al. Cellular and Mol. Immunology, 4th ed. (W.B. Saunders, Co., 2000). An antibody may be part of a larger fusion molecule, formed by covalent or non-covalent association of the antibody with one or more other proteins or peptides.

The terms "full length antibody," "intact antibody" and "whole antibody" are used herein interchangeably to refer to an antibody in its substantially intact form, not antibody fragments as defined below. The terms particularly refer to an antibody with heavy chains that contain an Fc region.

A "naked antibody" for the purposes herein is an antibody that is not conjugated to a cytotoxic moiety or radiolabel.

"Antibody fragments" comprise a portion of an intact antibody, preferably comprising the antigen binding region thereof. Examples of antibody fragments include Fab, Fab', F(ab')2, and Fv fragments; diabodies; linear antibodies; single-chain antibody molecules; and multispecific antibodies formed from antibody fragments.

"Fab" fragments: Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen. The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site. "Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv, see, e.g., Pluckthun, in The Pharmacology of Monoclonal Antibodies, vol. 113, Rosenburg and Moore eds., (Springer-Verlag, New York, 1994), pp. 269-315.

The monoclonal antibodies herein specifically include "chimeric" antibodies in which a fragment of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., PNAS USA 81:6851-6855 (1984)). Chimeric antibodies include PRIMATIZED® antibodies wherein the antigen-binding region of the antibody is derived from an antibody produced by, e.g., immunizing macaque monkeys with the antigen of interest.

"Humanized" forms of non-human (e.g., murine) antibodies are chimeric antibodies that contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a fragment of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992). See also the following review articles and references cited therein: Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, J. Mol. Biol., 227:381 (1991); Marks et al., J. Mol. Biol., 222:581 (1991). Also available for the preparation of human monoclonal antibodies are methods described in Cole et al., Monoclonal Antibodies and Cancer Therapy, Alan R. Liss, p. 77 (1985); Boerner et al., J. Immunol., 147(1):86-95 (1991). See also van Dijk and van de Winkel, Curr. Opin. Pharmacol., 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., PNAS USA, 103:3557-3562 (2006) regarding human antibodies generated via a human B-cell hybridoma technology.

An "antigen" is a predetermined moiety to which an antibody can specifically bind, herein it is CD166. The target antigen may be polypeptide, carbohydrate, nucleic acid, lipid, hapten or other naturally occurring or synthetic compound. Preferably, the target antigen is a polypeptide.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

2. Anti-CD166 Antibodies

Antibodies against the CD166 ligand disclosed herein can be produced using any of the methods known in the art. These methods of producing antibodies include immunizing a mammal (e.g., mouse, rat, rabbit, horse, goat, sheep or monkey) with the protein. Antibodies may be obtained from immunized animals using any of a variety of techniques known in the art, and screened, preferably using binding of antibody to antigen of interest. Commerically available anti-CD166 antibodies include the following: PE anti-human CD166 antibody (BioLegend, Cat No. 343903); Anti-CD166 antibody (Abcam, Cat Nos. ab109215, ab175428, ab206127, ab196846, ab78649); Anti-CD166 antibody C-terminal (Abcam, cat no. ab190755); and Anti-CD166 antibody (R&D Systems, Cat No. MAB656).

Various procedures known within the art may be used for the production of polyclonal or monoclonal antibodies directed against a polypeptide of the invention, or against derivatives, fragments, variants, analogs homologs or orthologs thereof. See, for example, ANTIBODIES: A LABORATORY MANUAL, Harlow and Lane (1988) Cold Spring Harbor Laboratory Press, Cold Spring Harbor, N.Y. Some of these antibodies are discussed below. Methods for making fully human monoclonal antibodies are described in CURRENT PROTOCOLS IN IMMUNOLOGY, Ed. John E Coligan, Barbara E Bierer, David H Margulies, Ethan Shevach, Warren Strober. 1994-2006 John Wiley & Sons, Inc. These methods are well-known in the art.

3. Monoclonal Antibodies

The term "monoclonal antibody" (mAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. mA.bs thus contain unique antigen-binding site capable of binding specifically with a particular epitope of the antigen. Thus, "monoclonal" antibodies are distinguished from "polyclonal" antibodies, which are a mixture of discrete antibodies that have multiple binding specificities.

Monoclonal antibodies can be prepared using hybridoma methods, such as those described by Kohler and Milstein (1975) Nature, 256:495 and by Goding, Monoclonal Antibodies: Principles and Practice, pp. 59-103 (Academic Press, 1986), the disclosures of which are hereby incorporated by reference.

Monoclonal antibody-producing hybridoma cells can be seeded and grown in a suitable culture medium that preferably contains one or more substances that inhibit the growth or survival of the unfused, parental myeloma cells. Preferred myeloma cells are those that fuse efficiently, support stable high level expression of antibody by the selected antibody producing cells, and are sensitive to a medium such as HAT medium. Culture medium in which the hybridoma cells are growing is assayed for the presence of monoclonal antibodies directed against the epitope of interest, i.e., CD166. Preferably, the binding specificity is determined by enzyme-linked immunoabsorbance assay (ELISA) or any similar assay known in the art. Once produced, antibodies or fragments thereof can be tested for recognition of the target polypeptide by standard immunoassay methods including, for example, enzyme-linked immunosorbent assay (ELISA) or radioimmunoassay assay (RIA). See, Short Protocols in Molecular Biology eds. Ausubel et al., Green Publishing Associates and John Wiley & Sons (1992).

The monoclonal antibodies of the current invention are those that specifically bind to CD166.

In a preferred embodiment, the monoclonal antibody has an affinity greater than micromolar (i.e. an affinity greater than $10^{-6}$ mol), which can be determined easily by those of skill in the art, for example, by Scatchard analysis, see Munson & Pollard, Anal. Biochem., 107:220, 1980.

4. Pharmaceutical Compositions Comprising ILT3, ILT3Fc or Anti-CD166

Pharmaceutical compositions of the invention may include ILT3 or ILT3Fc or a CD166-binding fragment thereof. Compositions for use identifying a CD166-expressing cancer include anti-CD166 antibodies or a CD166 binding fragment thereof. The pharmaceutical compositions of this invention may be in a variety of forms, which may be selected according to the preferred modes of administration. These include, for example, solid, semi-solid and liquid dosage forms such as tablets, pills, powders, liquid solutions or suspensions, suppositories, and injectable and infusible solutions. The preferred form depends on the intended mode of administration and therapeutic application. Modes of administration may include oral, parenteral, subcutaneous, intravenous, intralesional or topical administration. The compositions of this invention may, for example, be placed into sterile, isotonic formulations with or without cofactors which stimulate uptake or stability. The formulation is preferably liquid, or may be lyophilized powder. For example, the compositions or polypeptides of the invention may be diluted with a formulation buffer comprising 5.0 mg/ml citric acid monohydrate, 2.7 mg/ml trisodium citrate, 41 mg/ml mannitol, 1 mg/ml glycine and 1 mg/ml polysorbate This solution can be lyophilized, stored under refrigeration and reconstituted prior to administration with sterile Water-For-Injection (USP). The compositions of the present invention can also be formulated so as to provide slow or controlled-release of the active ingredient therein using, e.g., hydropropylmethyl cellulose in varying profragments to provide the desired release profile, other polymer matrices, gels, permeable membranes, osmotic systems, multilayer coatings, microparticles, liposomes and/or microspheres. In general, a controlled-release preparation is a composition capable of releasing the active ingredient at the required rate to maintain constant pharmacological activity for a desirable period of time. Such dosage forms can provide a supply of a drug to the body during a predetermined period of time and thus maintain drug levels in the therapeutic range for longer periods of time than other non-controlled formulations.

The pharmaceutical compositions of some embodiments are prepared for oral administration, preferably as solid compositions. However, the pharmaceutical compositions may be administered by intravenous injection or by injection or infusion into the prostate gland or prostate tumor, parenterally, or via an implanted reservoir. Sterile injectable forms of the pharmaceutical compositions may be aqueous or oleaginous suspensions. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium.

The pharmaceutical compositions employed in some embodiments may be orally administered in any orally acceptable dosage form, including, but not limited to, solid forms such as capsules and tablets. In the case of tablets for oral use, carriers commonly used include microcrystalline cellulose, lactose and corn starch. Lubricating agents, such as magnesium stearate, are also typically added. When aqueous suspensions are required for oral use, the active ingredient may be combined with emulsifying and suspending agents. If desired, certain sweetening, flavoring or coloring agents may also be added.

Oral compositions generally comprise an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be comprised as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

The invention may be present in the pharmaceutical compositions in the form of salts of pharmaceutically acceptable acids or in the form of bases. The therapeutic agents may be present in amorphous form or in crystalline forms, including hydrates and solvates. Preferably, the pharmaceutical compositions comprise a therapeutically effective amount.

Pharmaceutically acceptable salts of the therapeutic agents described herein include those salts derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate salts. Other acids, such as oxalic, while not in themselves pharmaceutically acceptable, may be employed in the preparation of salts useful as intermediates in obtaining pharmaceutically acceptable acid addition salts.

Salts derived from appropriate bases include alkali metal (e.g., sodium and potassium), alkaline earth metal (e.g., magnesium), ammonium and $N^+$ ($C_{1-4}$ alkyl)4 salts. It is anticipated that some embodiment include the quaternization of any basic nitrogen-containing groups of the therapeutic agents disclosed herein. Water or oil-soluble or dispersible products may be obtained by such quaternization.

C. Diagnostic Kits for the Detection of and Treatment of CD166 Expressing Cancer Cells The invention also provides for diagnostic kits comprising products and reagents for detecting in a sample from a subject the presence of CD166-expressing cancer cells. Some kits include labeled ILT3 or ILT3Fc, preferably labeled for visual detection, or other CD166-binding fragment of ILT3. In addition to ILT3 or ILT3Fc, an embodiment of the kit could include an anti-CD166 antibody or fragment thereof, including monoclonal (such as 2D9) and polyclonal antibodies, and optionally also secondary antibodies that are labeled for easy detection for example with a fluororphore or horseradish peroxidase enzyme. The labeling moieties can include compositions that can be detected by spectroscopic, photochemical, biochemical, bioelectronic, immunochemical, electrical, optical or chemical means as described herein. A typical kit includes a container containing the agent, such as ILT3Fc or an anti-CD166 antibody and appropriate secondary antibodies for detection.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items. elements or steps. Furthermore, the indefinite article "a" or "an" is meant to indicate one or more of the item, element or step modified by the article.

5. Examples

Example 1: Generation of Recombinant ILT3Fc

Methods for making ILT3Fc using, for example, recombinant technology or chemical synthesis, are described in detail in Cosman, U.S. Pat. No. 6,448,035 and are also described in Suciu-Foca et al., U.S. Pat. No. 8,207,110 and Suciu-Foca et al., U.S. Serial application Ser. No. 13/621,961.

Example 2: Generation of ILT3 Ligand Recognizing mAbs

In order to identify the ligand of ILT3Fc, a mAb-based strategy was used. Mice were immunized with the ILT3Fc-binding H9 cell line. The supernatants of hybridoma were screened for binding to T-cell Acute Lymphoblastic Leukemia (T-ALL) cell lines which showed ILT3Fc-FITC binding but not to resting CD3 T cells known to be ILT3Fc negative.

A hybridoma with these characteristics was selected for cloning and generation of mAbs. As shown in FIG. 1, each mAb was tested for its capacity to interfere with the inhibitory effect of various concentrations of ILT3Fc (from 12.5 to 50 ug/ml) which were added to MLC containing CD3 T cell from a healthy responder and APC from an unrelated stimulator. ILT3Fc inhibited the proliferation from 95% at the highest concentration to 82% at the lowest concentration. Some mAbs had an additive inhibitory effect, while others tended to attenuate the suppressive effect of ILT3Fc, suggesting that they may display agonistic or antagonistic activities.

Such antibodies as well as FITC-ILT3Fc were next screened by flow cytometry for binding to cells from a battery of 7 T-ALL cell lines (H9, Jurkat, CCRF-CEM, DND41, HH, All-SiL, HPB-ALL). As shown in Table1 below, one of these antibodies 2D9 (anti-CD166) showed the same pattern of binding like ILT3Fc.

TABLE 1

Screening of 8 T-ALL cell lines for cell surface binding of mAbs and ILT3Fc. The binding of each mAb and ILT3Fc-FITC was determined by Flow cytometry "−" corresponds to no or marginal binding, while "+" to positive binding and the positive signals of various intensity.

|  | Immune cell | H9 | Jurkat | CCRF-CEM | DND41 | HH | ALL-SiL | HPB-ALL |
|---|---|---|---|---|---|---|---|---|
| Neg. Ctl | None | − | − | − | − | − | − | − |
| 2E4 | H9 | + | − | − | − | N/A | − | − |
| 2D1 | U2OS | − | − | − | − | N/A | − | − |
| 1A5 | U2OS | − | − | +++ | − | N/A | − | − |
| 2E3 | H9 | + | − | − | − | − | − | − |
| 2D2 | H9 | +++ | − | − | − | +++ | − | − |
| 2D9 | H9 | + | + | + | + | + | − | + |
| ILT3Fc | − | +++ | ++ | +++ | ++ | + | − | − |

Antibodies from the screened hybridoma supernatants were purified and used for immuno-precipitation of the antigen they recognized the cell surface of H9, the immunizing cell line. As shown in Table 2 below, the resulting bands were mass-spectrometry analyzed and shown to recognize IMPDH2 (2E4), ERP5 (1A5), CD71 (2C1, 2C10 and 106) and CD166 (2D9).

TABLE 2

Summary of the specificity and isotype of 22 mAbs generated.

| ID | Name | Target Cell | Isotype | IPed | Epitope | Clone Name | Supernatant | To be IP | Stored in |
|---|---|---|---|---|---|---|---|---|---|
| 1 | 2E3 | H9 | IgG2a, Kappa |  |  |  |  |  |  |
| 2 | 2E4 | H9 | IgM | Y | IMPDH2 (Sequenced) |  | 500 mL |  |  |
| 3 | 2D2 | H9 | IgG2b, Kappa |  |  |  |  |  |  |
| 4 | 2D9 | H9 | IgG1, Kappa | Y(2) | CD166 (Sequenced) | 2D9E7F10 | 300 mL |  | E4JE4LE4K |
| 5 | 2D1 | U2OS | IgG1, Kappa | Y |  |  |  | Y | D2JD2I |
| 6 | 1A5 | U2OS | IgG2a, Kappa | Y | ERP5 (Sequenced) |  | 500 mL |  |  |
| 7 | 1H2 | H9 | IgM |  |  |  |  | Y | D3I |
| 8 | 1H3 | H9 | IgG2b, Kappa |  |  |  |  | Y | D2C |
| 9 | 2G8 | H9 | IgG1, Kappa |  |  |  |  | Y | D3I |
| 10 | 1B1 | Jurkat | IgG2b, Kappa |  |  |  |  |  |  |
| 11 | 1D2 | Jurkat | IgG2b, Kappa |  |  |  |  | Y | D2C |
| 12 | 1C5 | Jurkat | IgM |  |  |  |  |  |  |
| 13 | 2F1 | Jurkat | IgG2a, Kappa |  |  | 2F1A10C7 | 500 mL |  | D3LD2C |
| 14 | 2H6 | Jurkat | IgG2b, Kappa | Y | Sequenced | 2H6G10 | 500 mL |  | D2D |
| 15 | 2E10 | Jurkat | IgG2b, Kappa | Y | Sequenced | 2E10B2 | 500 mL | Y | D2D |
| 16 | 1D4 | Jurkat | IgG3, Kappa | Y |  | C11E2 | 500 mL |  | D3K |
| 17 | 2C10 | Jurkat | IgG3, Kappa | Y | CD71 By WB | 2C10H11H7 | 500 mL |  |  |
| 18 | 2C11 | Jurkat | IgG1, Kappa | Y | Sequenced | 2C11D6 | 500 mL | Y | D3J |
| 19 | 2D1 | Jurkat | IgG2b, Kappa |  |  |  |  |  |  |

TABLE 2-continued

Summary of the specificity and isotype of 22 mAbs generated.

| ID | Name | Target Cell | Isotype | IPed | Epitope | Clone Name | Supernatant | To be IP | Stored in |
|----|------|-------------|---------|------|---------|------------|-------------|----------|-----------|
| 20 | 1C6 | Jurkat | IgG2a, Kappa | Y | CD71 By WB | 1C6B2C7 | 500 mL | | |
| 21 | 2C1 | Jurkat | IgG2b, Kappa | Y | CD71 (Sequenced) | 2C1E2G3 | 500 mL | | |
| 22 | 2B2 | Jurkat | IgG2b, Kappa | | | | | Y | D3K |

Generation of 2D9 mAb:

Six- to 8-wk-old female BALB/c mice were given four i.p. injections of 1×10⁶ H9 cells in PBS. Mice were sacrificed 3 days after the last injection. Splenocytes were isolated and fused with a mouse myeloma fusion partner, Sp2/0-Ag14 (American Type Culture Collection), using 50% (w/v) polyethylene glycol (Sigma-Aldrich, St Louis, Mo.). Supernatants from hybridoma cultures were screened by flow cytometry for binding to the immunogen (H9 cells) but not to purified resting human T cells. Supernatants from hybridomas fulfilling this criteria, were further tested for their capacity to revert the inhibitory activity of ILT3.Fc (12.5 ug/ml) in MLC. Hybridoma which enhanced T cell proliferation in medium containing ILT3.Fc were cloned and expanded for immunoprecipitation studies. The 2D9 mAb was first immobilized to the surface of protein G beads and then incubated with H9 cell lysate overnight. After intensive wash, the immuno-complex was eluted and subjected into the SDS-PAGE gel separation. mAb 2D9 (IgG1, kappa) immunoprecipitated a 100 kD protein which was shown by mass spectrometry to have the CD166 sequence.

Accordingly, another embodiment pertains to an anti-CD166 antibody or CD166 specific fragment thereof produced by immunizing a mouse with ILT3Fc binding H9 T-cells, producing hybridomas from immune cells harvested from the immunized mouse (or other suitable non-human mammal host, e.g. rabbit, goat, rat, pig, etc.); and screening antibodies from the hybridomas for binding to CD166. In a specific example, the screening is conducted by immunoprecipitation against H9 T-cell antigens and identifying antibodies that bind to CD166 present on or obtained from H9 T-cells. Immunoprecipitation may occur by immobilizing antibody to a support surface (such as a bead) before or after contact with antigen to isolate antigen/antibody complex. The antigen bound to a given antibody can be analyzed by known techniques including, but not limited to, mass spectrometry, or correlating or competitive binding studies using commercially available antibodies against CD166. As noted in the above table, the epitope of antibody 2D9 is CD166.

Example 3: ILT3Fc Binds to CD166-Positive Population of Activated T Cells

Figures 2A, 2B:
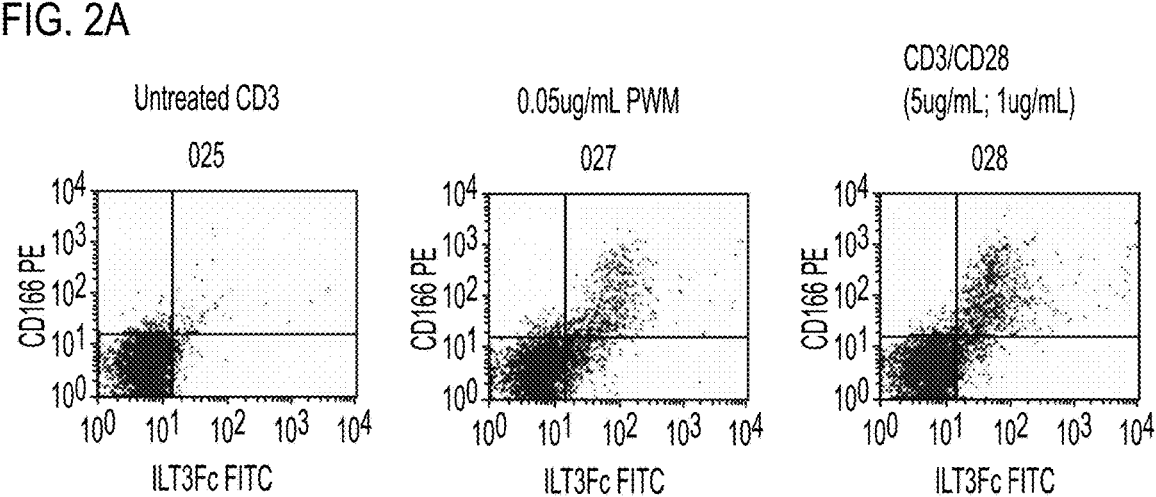
FIG. 2A-2B are graphs that illustrate the binding of ILT3Fc to the CD166-positive population of activated T cells.

In order to test if CD166 is the ligand of ILT3Fc, anti-CD166 PE and ILT3Fc-FITC double staining of PMA or CD3 plus CD28 antibody-triggered CD3+ T cells from healthy individuals was performed. As shown in FIG. 2, ILT3Fc bound to CD166-positive cells, indicating that they were co-expressed. When the cells were triggered in the presence of ILT3Fc, the ILT3Fc binding was obviously inhibited. CD166 expression by the same ILT3Fc-treated cells, was also inhibited indicating a positive correlation between ILT3Fc binding and CD166 expression.

Example 4: KD and Over Expression Experiments

Figure 3A:
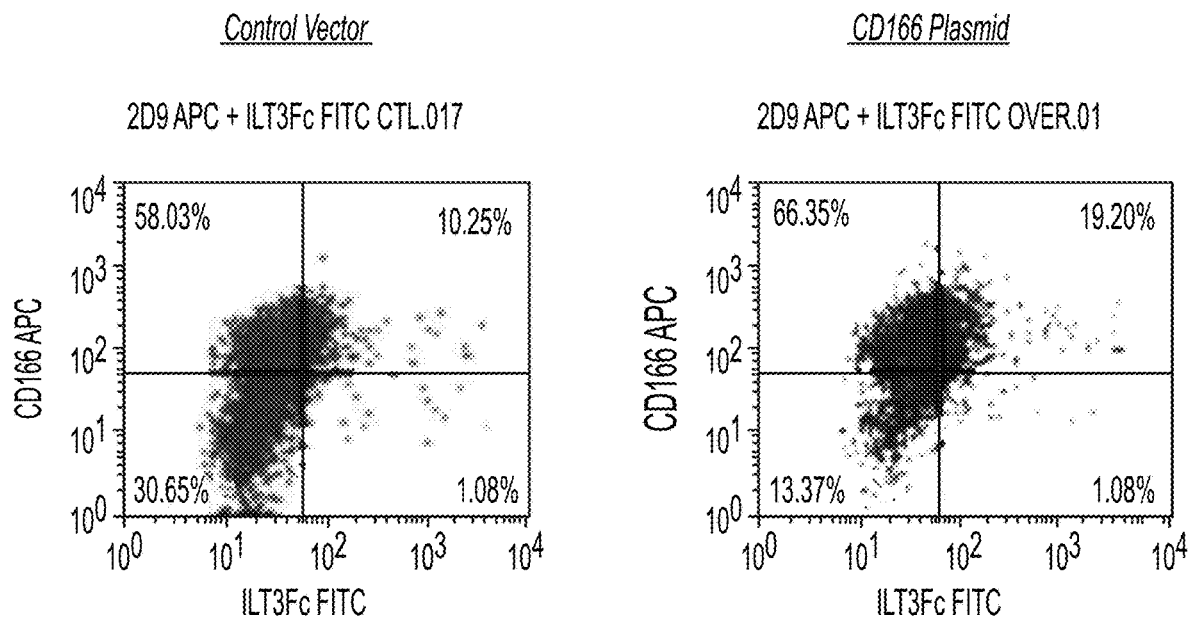
FIG. 3A-3B are graphs that illustrate knocking down of CD166 decreases while over-expression of CD166 increases ILT3Fc binding.
Figure 3B:
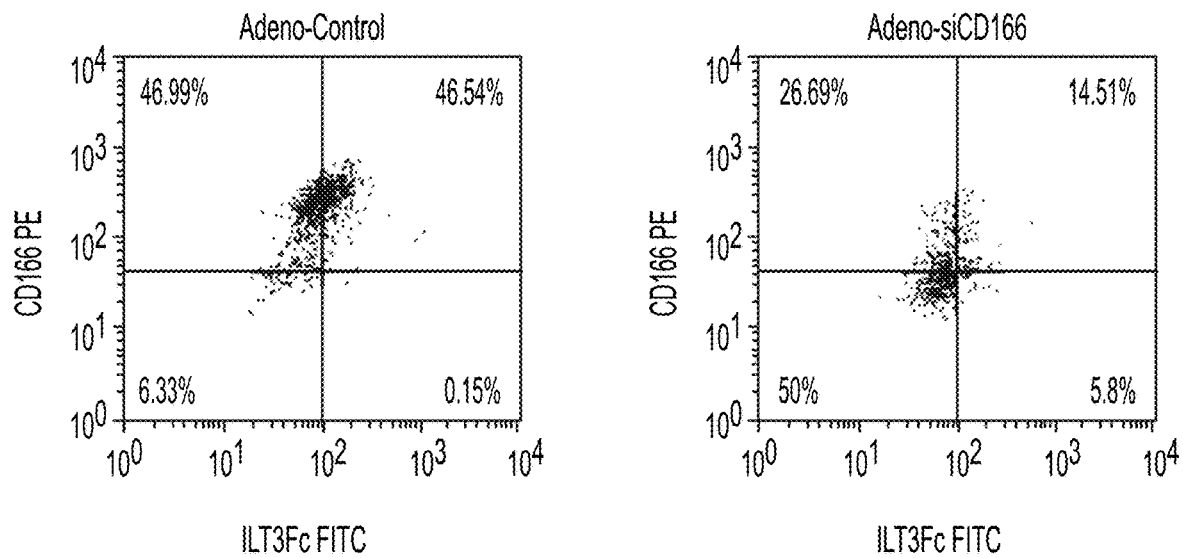

In order to determine if CD166 is the ligand of ILT3Fc, KD experiments of CD166 using adeno-virus carrying CD166 specific short hair RNA were performed. As shown in FIG. 3, the ILT3Fc binding decreased from 46% in the control-virus infected H9 cells to less than 20% in the CD166 KD cells. At the same time, to determine whether CD166 overexpression results in increased binding of ILT3Fc, tumor cells were transfected with a full length CD166 plasmid. Flow cytometry study showed that ILT3Fc binding increased significantly upon CD166 over-expression (FIG. 3). Taken together, the data indicate that CD166 expression is positively correlated with the ILT3Fc binding to the tumor cells.

Figure 4:
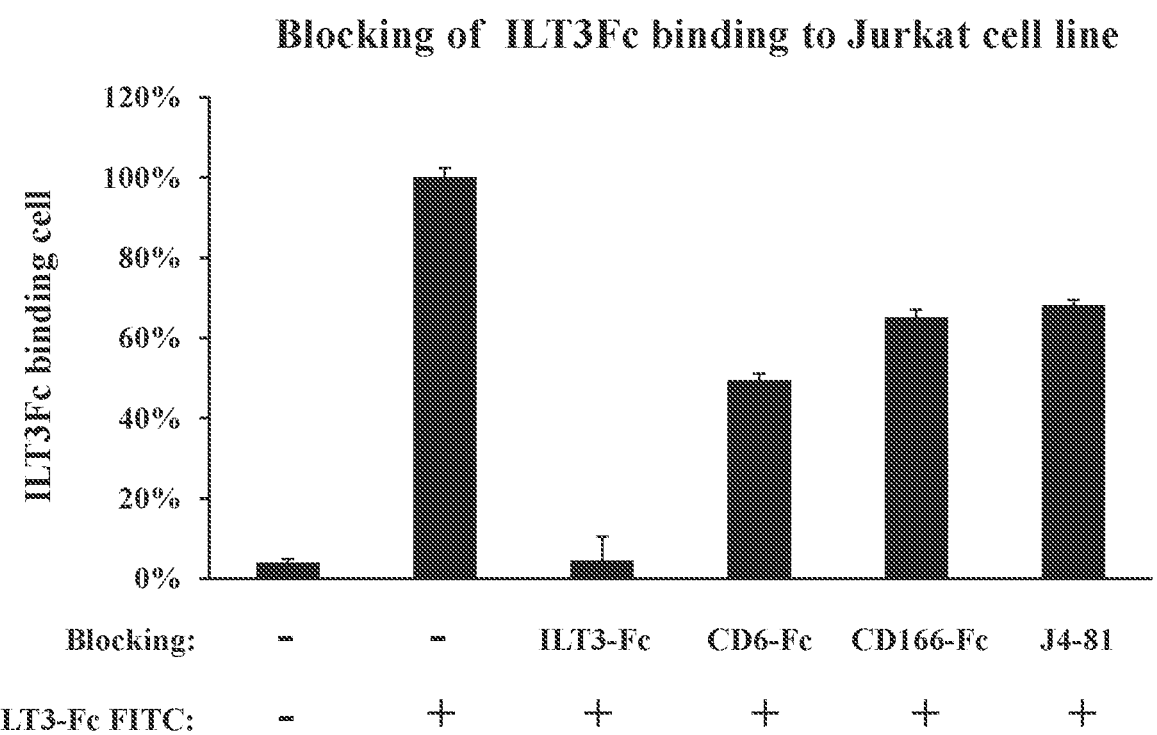
FIG. 4 is a graph that represents ILT3Fc binding to Jurkat cells following incubation with unlabeled ILT3Fc, CD6.Fc, CD166.Fc or anti CD166 antibody J4-81. The percentage of cells binding ILT3Fc was inhibited specifically by unlabeled ILT3Fc (positive control). Partial inhibition of binding occurred after pretreatment with CD6.Fc, CD166.Fc and anti-CD166 mAb (J4-81).

Example 5: Some Known CD166 Involved Protein-Protein Interaction Partially Block the ILT3Fc Binding CD166 protein-protein interactions include homophilic interaction with CD166 itself and heterophilic interaction with CD6. To determine whether these two types of interactions interfere with ILT3Fc binding to T-ALL, flow cytometry studies were performed. As shown in FIG. 4, ILT3Fc-FITC binding to target Jurkat cells was almost completely blocked when cells were pre-incubated with unconjugated "cold" ILT3Fc, indicating the binding specificity is high. Pre-incubation with CD6-Fc, CD166-Fc or anti-CD166 mAb (J4-81) partially inhibited the binding of ILT3Fc-FITC to Jurkat cells by 49%, 30% and 28% respectively. This result suggests that ILT3Fc may share some binding site(s) on the CD166 molecule with CD6 or CD166 itself.

Example 6: ELISA Studies

The direct interaction of ILT3Fc with CD166, was further documented in ELISA assays. 96 well plates were pre-coated overnight at 4 degree Celsius with increasing doses (2 ug, 4 ug, 8 ug and 16 ug/mL) of human IgG1, human CD6-Fc or Human ILT3Fc. Plates were washed with TSM BUFFER and then coated for 2 hours at 4 degree Celsius with BSA to block non-specific binding. After washing with TSM buffer, full length human CD166 protein or human CD166Fc were added to parallel rows. After 2 hours of incubation at 4 degree Celsius, anti-CD166 antibody were added to all wells to detect binding. As shown in FIG. 5, the results showed dose dependent increase of CD166 binding to ILT3Fc coated wells. Binding of CD166 protein to CD6 coated wells used as the positive control was very strong. In contrast, there was no binding to IgG coated wells used as a negative control. Therefore, both full length CD166 and CD166-Fc bind to ILT3Fc in a dose-dependent manner, further suggesting that CD166 is the ligand of ILT3.

Example 7: ILT3Fc Binding is Associated with CD166 Expression on Tumor Cell Lines Numerous antibodies to CD166 are commercially available. Some of them bind to the distal immunoglobulin domains (D), such as J4-81. Others to the membrane proximal constant region (C) of this molecule such as AZN-L50 (12). As shown in Table 3, when ILT3Fc binding and CD166 expression on tumor cell lines were detected by different antibodies, a similar pattern was found: Most T-ALL as well as the SK-MEL-1 melanoma cell line bound ILT3Fc and showed CD166 expression when stained with antibodies to the D region. However, one T-ALL line (ALL-SiL) as well as the K562 cell line showed only marginal ILT3Fc binding and their CD166 expression could only be detected by antibodies to the C region. The ILT3Fc binding site, therefore, appears to be located primarily within the D domain of CD166. Acute B cell leukemia line, named B3HR is another tumor cell line that expresses CD155.

TABLE 3

Immunofluorescence binding pattern of antibodies to the D domain (3A6) and C domain (AZN-L50) of CD166 and of ILT3Fc-FITC to 7 different T-ALL, one melanoma line (SK-MEL-1) and myelogenous leukemia (K562).

| Name | Jurkat | ALL-SIL | HH | CCRF-CEM | SK-MEL-1 | HPE-ALL | DND-41 | H9 | K562 |
|---|---|---|---|---|---|---|---|---|---|
| Cell Type | T cell leukemia | T cell leukemia | T cell lymphoma | T cell leukemia | Melanoma | T cell leukemia | T cell leukemia | T cell lymphoma | Leukemia |
| Disease | T cell acute lymphoblastic leukemia | T cell acute lymphoblastic leukemia | Cutaneous T cell lymphoma | T cell acute lymphoblasitc leukemia | Malignant Melanoma | T cell acute lymphoblastic leukemia | T cell acute lymphoblastic leukemia | Cutaneous T cell lymphoma | Chronic myelogenous leukemia |
| Species | Human (*Homo sapiens*) | Human (*Homo sapiens*) | Human (*Homo sapiens*) | Human (*Homo sapiens*) | Human (*Homo sapiens*) | Human (*Homo sapiens*) | Human (*Homo sapiens*) | Human (*Homo sapiens*) | Human (*Homo sapiens*) |
| CD166 (3A6) | ++ | − | ++ | ++ | ++ | ++ | ++ | +++ | − |
| CD166 (AZN-L50) | N/A | + | N/A | N/A | N/A | N/A | N/A | ++ | + |
| ILT3Fc-FITC | ++ | +/− | + | +++ | ++ | + | ++ | +++ | +/− |

Example 8: ILT3Fc Inhibits the Growth of Multiple Types of Malignant Cell Lines

Based on the previous evidence that CD166 is the ligand of ILT3 and that they are co-expressed on T-ALL, the effect of ILT3Fc on tumor cell growth in vitro was analyzed. Cells from 10 cell lines were seeded in the presence of various concentrations of ILT3Fc (0 to 50 ug/ml). Cell growth and viability were measured at 72 hours by CCK-8 cell counting assay, trypan blue exclusion, CFSE flow cytometric analysis, Annexin V/PI staining, and tritiated thymidine incorporation methods. All the data showed that ILT3Fc strongly inhibited (by 50 to 90%) the growth of all tumor cell lines tested (FIG. 6A-6E and FIG. 7). Both trypan blue and PI staining showed that there was no direct cytotoxic effect. Instead, there was early apoptosis in a large segment of the ILT3Fc treated tumor cell (FIG. 8).

Example 9: Flow Cytometry Method for Assaying the Expression of ILT3L Using Unlabeled ILT3Fc and a Labeled Secondary Reagent with Specific Affinity for ILT3Fc Bone marrow aspirate including peripheral blood mononuclear cells from patients with T-ALL or cultured T-ALL cell lines were incubated with 10 µg of unlabeled ILT3Fc for 30 minutes at 4° C. in 100 µl of staining buffer. The staining buffer consisted of Tris buffered saline (TBS), 1-3 mM $Mn^2$, and 1% BSA or a similar formulation. Of note, ILT3Fc is preferably dissolved in a buffer compatible with the staining buffer used. Cells were washed three times in staining buffer. An appropriate negative control consisted of the same type of cells incubated with buffer alone (no ILT3Fc) or 10 µg human IgG during the first step.

The cells were then incubated with a secondary reagent (such as anti-Human ILT3 antibody) that binds to the ILT3 in the probe, wherein the secondary reagent is conjugated to a fluorophore such as PC5) for (30 minutes, 4° C.) and then washed three more times in staining buffer. Any antibody (or biologically active fragment or variant thereof) that specifically binds to ILT3 can be used as a secondary reagent. Commercially available monoclonal anti-human ILT3 monoclonal antibodies were used. Monoclonal anti-human ILT3 antibodies (designated A, B, C and D) that were made in the lab by immunizing mice with ILT3Fc were also tested (details for making anti-human ILT3 mAb are set forth in Example 3). Commercially available anti-ILT3 antibodies from R&D Systems include:

| Human ILT3/CD85k | Affinity Purified Polyclonal | Polyclonal Ab, Goat IgG |
|---|---|---|
| FC | AF2425 | 100 µg |
| Human ILT3/CD85k | Biotinylated Affinity Polyclonal | Purified PAb, Goat IgG1 |
| FC | BAF2425 | 50 µg |
| Human ILT3/CD85k<br>Human ILT3/CD85k | MAb (Clone mAB2425 100 µg 293622), Mouse IgG2A<br>mAb (Clone 293623), Mouse IgG2A | |
| FC | FAB24251P | |

*FC in the table above means flow cytometry tested.

stranded-DNA primers (Guides 3 and 4). For Designing of primers, the online tool provided by Zhang et al (43) was used. DNA primers with scores higher than 75 were selected to avoid the possible off-target effects.

Sequences of these primers are shown as follows:

| | |
|---|---|
| Guide 1 Forward:<br>CACCGAATTTTTAGGAAAAGCCCGA | SEQ ID NO: 1 |
| Guide 1 Reverse:<br>AAACTCGGGCTTTTCCTAAAAATTC | SEQ ID NO: 2 |
| Guide 2 Forward:<br>CACCGTGAGGCACCTACAATAGTCA | SEQ ID NO: 3 |
| Guide 2 Reverse:<br>AAACTGACTATTGTAGGTGCCTCAC | SEQ ID NO: 4 |
| Guide 3 Forward:<br>CACCGCTATAGCAGGTATCTATATA | SEQ ID NO: 5 |
| Guide 3 Reverse:<br>AAACTATATAGATACCTGCTATAGC | SEQ ID NO: 6 |
| Guide 4 Forward:<br>CACCGCTCTGTAGTGTCTCTATAGC | SEQ ID NO: 7 |
| Guide 4 Reverse:<br>AAACGCTATAGAGACACTACAGAGC | SEQ ID NO: 8 |

The double stranded guide DNA (Guides 1-4) was first cloned individually into the BsmB1 site of a lentiCRIPRv2

Example 10: Knockout Expression of CD166 by CRISPR Mediated Genomic Editing of CD166 Genome Recent advance in genome editing (39-41) via introduction of double strand breaks (DSBs) on a target gene allows us to address the question if a given candidate protein is ILT3Fc ligand. A significant advantage of using the CRISPR/Cas9 system (review in 41) to induce DSB in genomic DNA is its high level of efficiency. It was decided to use the double target guide RNA lentiviral system developed by GeCKO (42) to knockout CD166 gene. The backbone of this system is LentiCRSPRv2 vector, which encodes an U6 RNA promoter, SpCas9 ribonuclease and a puromycin resistance gene. Using lentiviral infection system allows us to target the genomic locus of CD166 in any given cell line; in this method, cells containing CD166 KO genomic can be selected for puromycin resistance. After carefully scanning the genomic locus, it was decided to target the exon 3, which encodes for all 5 known CD166 transcript variants. To ensure successful targeting on this region of genomic locus, we designed two upstream double stranded-DNA primers (Guides 1 and 2) and two downstream double vector to generate 4 recombinant (Guide 1-4 lentiCRIPRv2) plasmids, which encodes the U6 RNA promoter, SpCas9 ribonuclease and puromycin resistance gene. Seventy two hours after transfection, supernatants of cultures were collected. The four individual recombinant lentiviral particles (Guide 1-4 lentiCRIPRv2) were concentrated by PEG8000 precipitation of supernatants. To knockout the CD166 gene, Jurkat or H9 T cells were spin infected for two hours at room temperature with lentiviral particles which targeted two different genomic regions of exon three. These cells were incubated for an additional 72 h at 37° C. and then cultured for one week in medium containing puromycin (1-4 ug/ml). CD166-negative surviving tumor cells were sorted in 96 well trays by flow cytometry and cloned.

The combinatory of lentiviral particles for co-infection is shown as follows

Guide 1 and Guide 3 (Guide 1/3)
Guide 1 and Guide 4 (Guide 1/4)
Guide 2 and Guide 3 (Guide 2/3)
Guide 2 and Guide 4 (Guide 2/4)

One week after puromycin selection, the resistant cells were sorted for CD166 negative by flow cytometry and single clone of CD166 negative cells were tested by genomic PCR. We used following primers for genomic screening.

| | |
|---|---|
| Forward:<br>TTGCCCAAAATATCCAAACC | SEQ ID NO: 9 |
| Reverse:<br>GCTCACGACATTTTTACATGACA | SEQ ID NO: 10 |

The expected size of PCR DNA fragment from the wild type is 960 bp. The expected size of that from CD166 knockout cells, using either Guide 1/3 or Guide1/4, is around 700 bp; the expected size of that from CD166 knockout cells, using either Guide 2/3 or Guide2/4, is around 820 bp. The CD166 knockout cells were further confirmed by DNA sequencing from both ends.

Example 11: Loss of CD166 Expression Decreases ILT3Fc Binding to Jurkat Cells To further demonstrate that CD166 is the ligand of ILT3, a CRISPR-Cas9 system based genome editing tool was used to generate CD166 knock-out cell lines (CD166KO H9 and CD166KO Jurkat). As shown in FIG. 9(A)-9(B), flow analysis data confirmed that a CD166 negative H9 and Jurkat knock-out lines were successfully generated. Genomic DNA sequencing data also confirmed that the expected region was deleted. The ILT3Fc binding capacity of the knock-out line was tested and the data showed that loss of CD166 expression resulted in a dramatic decrease of ILT3Fc binding to H9 and Jurkat cells (FIG. 9(A)-9(B).

Example 12: ILT3Fc Induced Apoptosis in Wild-Type Over CD166 Knockout Jurkat Cells It has been shown that ILT3Fc inhibits Jurkat cell proliferation through inducing apoptosis. The susceptibility to apoptosis of the CD166 KO Jurkat cell lines was examined. WT Jurkat wild-type and CD166 KO Jurkat were left untreated or treated with 12.5 µg/ml of ILT3Fc or human IgG used as a negative control. Two days after the treatment, apoptosis was analyzed by Annexin-V/PI based assay (FIG. 10B). Cells were stained with Annexin V-FITC/PI kit according to the manufacturer's instruction (BD Biosciences). Briefly, cells were washed twice with ice-cold PBS and re-suspended in 1× Annexin-binding buffer at a concentration of 1×10$^6$ cells/ml. 5 µL of Annexin V-FITC and 5 µL of PI were added to each 100 µL of cell suspension. After 15 min incubation in the dark, 400 µL 1X Annexin V-binding buffer was added and cells were analyzed by flow cytometry. As shown in FIG. 10B, ILT3Fc treated WT H9 and Jurkat cells showed a notable portion of apoptotic cells. In contrast, the size of population of ILT3Fc treated CD166 KO Jurkat cells undergoing apoptosis was similar to that seen in the non-treated or IgG treated samples. This indicates that CD166 KO renders the cell's resistance to ILT3Fc induced apoptosis.

Figure 11:
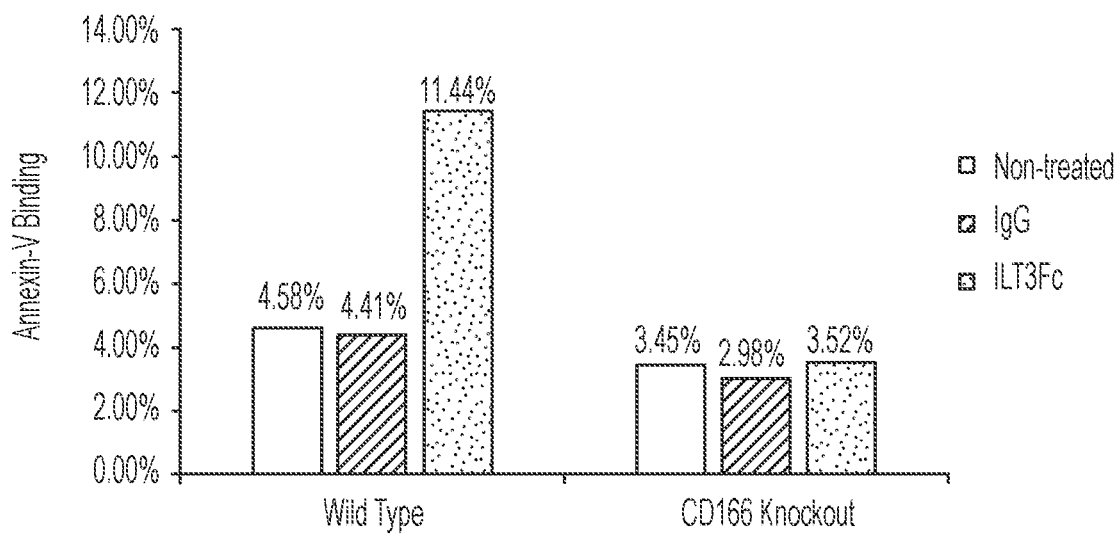
FIG. 11 is a bar graph that illustrates a CD166 knockout line insusceptible to ILT3Fc induced cell death.

Example 13: CD166 Knockout Line Becomes Insusceptible to ILT3Fc Induced Cell Death Cell viability in ILT3Fc treated WT Jurkat and CD166 KO Jurkat was also determined. For this, 0.25×10$^6$ of WT or CD166 KO Jurkat cells were left untreated or cultured in the presence of 12.5 ug/mL of ILT3Fc in 24-well plate. Three days after the treatment, viable cells were counted using a Trypan-blue exclusion assay. Viability was calculated from the formula: No. of viable cells in ILT3Fc treated/No. of viable cells in untreated sample. As shown in FIG. 11, the cell viability was significantly lower in ILT3Fc treated compared to the non-treated control samples.

The findings that loss of CD166 expression abrogates ILT3Fc binding to Jurkat cells and that CD166 KO renders the cell's resistance to ILT3Fc induced apoptosis and cell death demonstrate that CD166 is the ligand of ILT3Fc.

Also available is the antibody from Beckman Coulter IOTest® CD85k (ILT3)-PC5 PN IM3579; Item No: A46529.

A flow cytometry instrument and the appropriate acquisition/analysis software, such as BD Biosciences' FACSCalibur and Cell quest software, were used to analyze the ILT3Fc binding shown in FIGS. 1-4. T-ALL cell lines were expanded and maintained in culture. (FIG. 2 (A)-(B)). Gating identifies leukemic cells in bone marrow aspirate from a patient with T-ALL are shown in FIG. 1 (A)-(B). On the other hand, normal T cells from healthy individuals expressed low or no ILT3L (FIGS. 3 (A)-(B)-4 (A)-(B)). CD4-gated T helper cells form a healthy blood donor expressed 1% ILT3Fc binding (FIG. 3 (A)-(B)). CD3-gated T cells from a healthy blood donor also expressed low ILT3Fc binding at 12%. (FIG. 4 (A)-(B)).

The data generated by flow-cytometers can be plotted in a single dimension, to produce a histogram, or in two-dimensional dot plots or even in three dimensions. The regions on these plots can be sequentially separated, based on fluorescence intensity, by creating a series of subset extractions, termed "gates" or "gating."

The number of labeled cells, and optionally also the amount of label per cell, can be determined in different ways that depend on the reporter molecule. A preferred embodiment is using a fluorescent label and flow cytometry that can determine both the number of T-cells in a sample and amount of label per T-cell. Flow cytometry allows for the counting and examining of cells by suspending them in a stream of fluid and passing them by an electronic detection apparatus. This technique allows for the simultaneous analysis of the physical and/or chemical characteristics of up to thousands of particles per second in real time. Data accumulated using the flow cytometer can be analyzed using commercially available software.

Example 14: ILT3Fc Inhibits Tumor Proliferation in Lymphoma In Vivo Model

Examples provided supra present extensive data demonstrating ILT3Fc's anti-tumor proliferation activity in vitro. ILT3Fc was then tested for its anti-tumor proliferation effect in vivo.

Method:

Cutaneous T cell lymphoma H9 cells were transplanted into the NSG mice which is the most commonly used model in the anti-tumor study. The mice were then randomly selected into two groups to receive either ILT3Fc treatment or control treatment with human IgG. Following the treatment, the mice body weight, tumor burden as evaluated by bioluminescence image or solid tumor volume were monitored. More specifically, 7-10 weeks old NOD/SCID/IL2 receptor null (NSG) female mice (TACONIC, Hudson, N.Y.) were used and maintained under specific pathogen-free conditions. Experiments were performed in compliance with institutional guidelines as approved by the Institutional Animal Care and Use Committee of Columbia University.

Wild type and CD166 KO cells from the H9 cutaneous T cell lymphoma were infected with lentivirus expressing luciferase (FUW-Puro-Luciferase)(12). Luciferase expressing H9 cutaneous T cell lymphoma (5×10$^6$ cells/mouse) was injected subcutaneously (s.c) on the left flank. Tumor cell growth in ILT3.Fc treated mice and in control mice receiving an equal dose of human IgG were evaluated by in vivo bioimaging with the In vivo Imaging System (IVIS, Xenogen) and FACS analysis of human CD45+ cells. Treatment was initiated when tumor growth was visualized by bioluminescence. The volume of s.c growing tumors was assessed using the two largest perpendicular axes (1, length; w, width) using the formula Volume=$0.5*1*w^2$.

Figure 12:
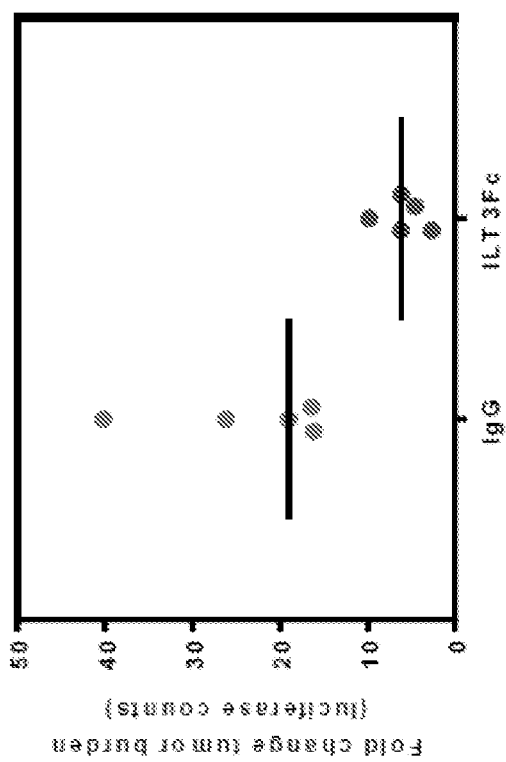
FIG. 12 is a graph that illustrates that tumor burden is reduced in NSG mice transplanted with T cell lymphoma H9cells treated with ILT3Fc compared to control (IgG).
Figure 13:
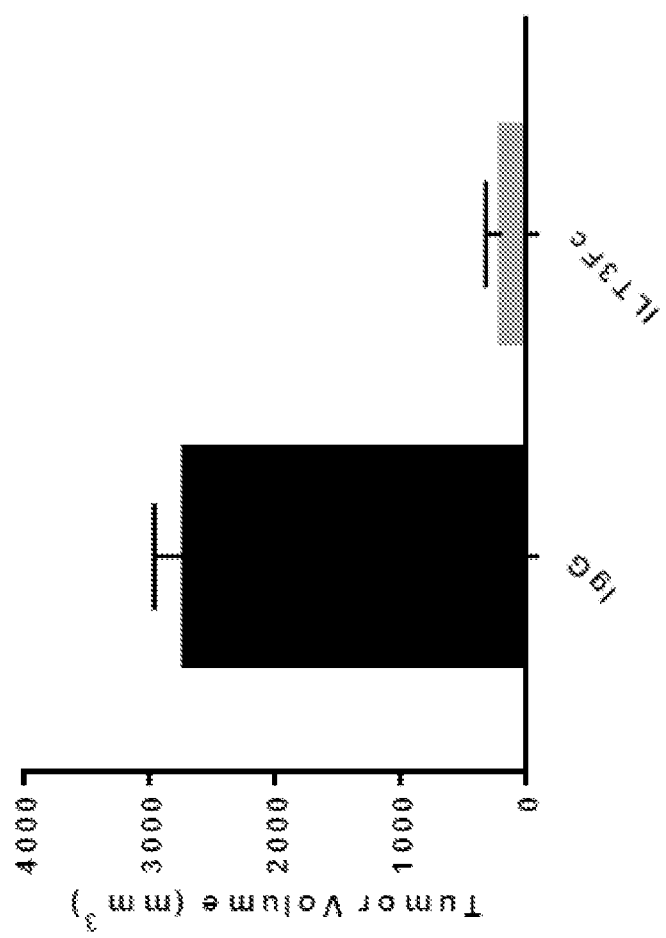
FIG. 13 is a bar graph that illustrates that tumor volume is reduced in NSG mice transplanted with T cell lymphoma H9cells treated with ILT3Fc compared to control (IgG).
Figure 14:
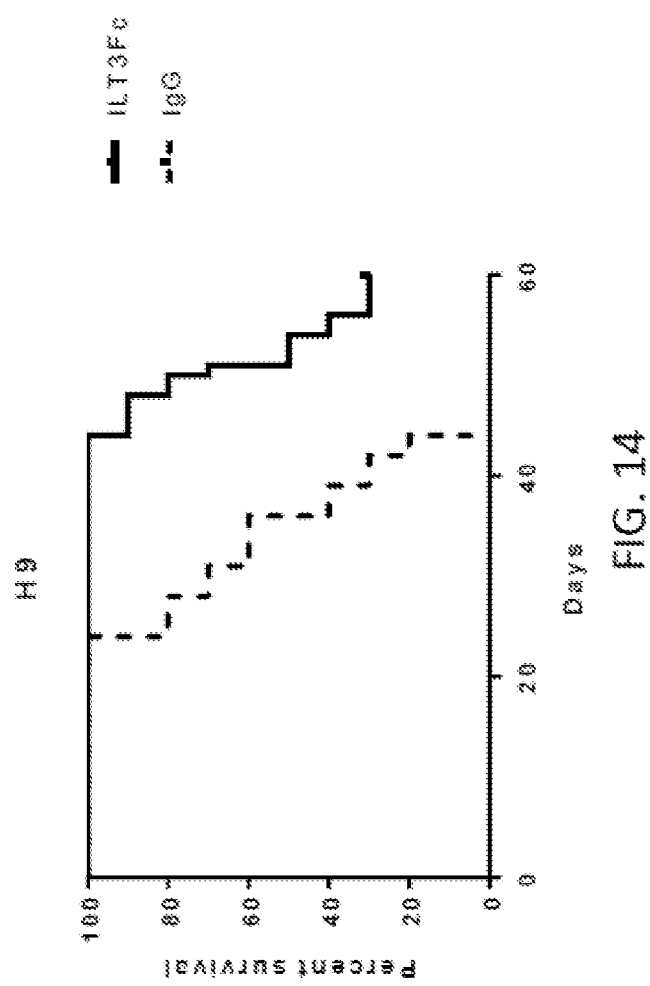
FIG. 14 shows a graph demonstrating that survival rates in NSG mouse lymphoma model increased in ILT3Fc treated mice versus control mice.

Results:

In contrast to the control treatment with common human IgG, the treatment with ILT3Fc significantly inhibited the tumor proliferation as shown by the tumor burden change in the FIG. 12. Secondly, the formed solid tumor volume is significantly smaller than that of in the control treated group as shown in FIG. 13. Finally, the ILT3Fc treatment remarkably increased the survival percentage as shown in the FIG. 14.

Conclusion:

In addition to the potent in vitro anti-tumor effect of ILT3Fc, it is demonstrated here that ILT3Fc also possesses potent in vivo anti-tumor growth effect.

Example 15: ILT3.Fc Mediates Effects Via p70S6K Signaling Pathway

To understand the mechanism underlying the ILT3.Fc effect on TCL, gene expression profiling of ILT3.Fc-treated and non-treated Jurkat cells was performed and analyzed by the DeMAND algorithm (Detecting Mechanism of Action by Network Dysregulation) (16). Of the 14,376 genes listed in order of the statistical significance of induced perturbations, RPS6KB1 ranked first. RPS6KB1 is a kinase that phosphorylates the S6 ribosomal protein inducing protein synthesis and controlling cell growth during GI to S transition phase. Some high ranking genes from the DeMAND list encode proteins involved in upstream signaling pathways targeting p70S6K. These include Rafl, MEK1, MAPK13, PLC gamma, PIK3R3, PDK1, and PP2A (17-23). Phosphorylation by ERK1 and ERK2 which belong to RAF1/MEK/MAPK signaling pathway and of PDK1 are also known to result in the activation of p70S6K (24, 25).

To investigate the effect of ILT3.Fc on signaling transduction from PLC gamma1 to MAPK and p70S6K, we analyzed their phosphorylation level in ILT3.Fc-treated wT/Jurkat cells by Western Blot. Cells were washed twice with ice-cold PBS at pH 7.4 and spun down at 2,000 rpm for 10 min. The pellet was re-suspended in lysis buffer (25 mM Tris-HCl pH 7.4, 150 mM NaCl, 1% NP-40, 1 mM EDTA, 5% glycerol) and incubated on ice for 10 rains with periodic mixing. Cell debris in lysates were removed by centrifugation at 13,000×g for 15 minutes at 4° C. before subjected to SDS-PAGE and transferred to nitrocellulose membranes. After blocking for 30 mins with 5% non-fat milk at room temperature, the membrane was immunoblotted with primary antibodies overnight at 4° C. Next day the membrane was incubated with horseradish peroxidase-conjugated secondary antibodies for 30 mins at room temperature and developed via enhanced chemiluminescence (ECL). The Bradford assay was used to determine protein content (Bio-Rad). All antibodies below were purchased from Cell Signaling Technology: P-p70S6 kinase (T389) Rabbit polyclonal Cat #9205S; P-NF-kappaB p65 (S536) clone:93H1 Rabbit mAb Cat #3033S; NF-kappa p65 clone:D14E12 Rabbit mAb Cat #8242P; Anti-Rabbit IgG HRP-Linked antibody Cat #7074; PLCgamma1 antibody Rabbit polyclonal Cat #2822; P44/42 MAPK (Erk1/2) clone:137F5 Rabbit mAb Cat #4695; Phospho-PLCgamma1 (Tyr783) Rabbit polyclonal Cat #2821S; Phospho-p42/44 MAP kinas (Thr202/Tyr204) Rabbit polyclonal Cat #9101; anti-Mouse IgG HRP-Linked antibody Cat #7076S; 3-Actin (8H10D10) Mouse mAb Cat #3700.

Figure 15A:
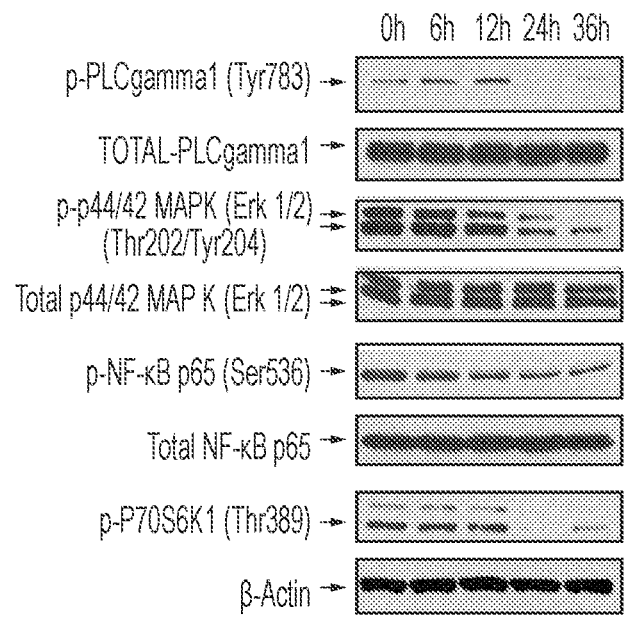
FIG. 15A-B Inhibition of p70S6K signaling pathway by ILT3.Fc.

PLC gamma1, MAPK and p70S6K were constitutively phosphorylated in wT/Jurkat cells. However, they were dephosphorylated within 24 hours of incubation in medium containing ILT3.Fc (FIG. 15A) Similar results were obtained by Western Blot analysis of H9 TCL.

Figure 15B:
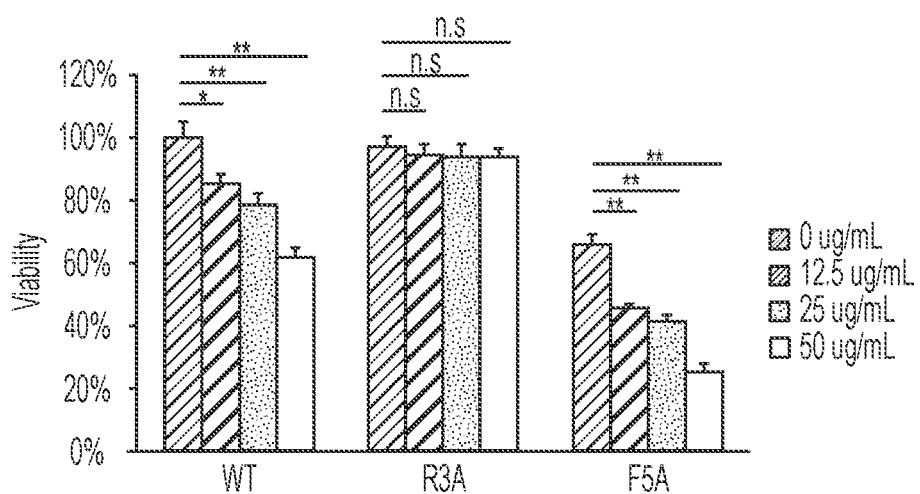

The central role of p70S6K was further confirmed by transfecting wT/H9 cells with S6K plasmids encoding wild-type (WT control), kinase dead (F5A) and constitutively-active (R3A) mutants (26, 27). Compared to the WT control, the constitutively-active S6K1 plasmid (R3A) rescued wT/H9 cells from ILT3.Fc-induced growth inhibition and cell death while the kinase-dead S6K1 plasmid (F5A) had no protective effect (FIG. 15B).

These findings indicate that p70S6K is a master effector of ILT3.Fc-induced perturbations, confirming numerous studies which demonstrated that while activation by various upstream pathways is important for tumor cell growth, inhibition of p70S6K signaling suppresses proliferation. Inhibition of NF-kB activity was also detected, consistent with blockade of tumor cell growth (28).

References Related To Example 15

16. Woo, J. H., et al. Elucidating Compound Mechanism of Action by Network Perturbation Analysis. Cell 162, 441-451 (2015).
17. Lehman, J. A. & Gomez-Cambronero, J. Molecular crosstalk between p70S6k and MAPK cell signaling pathways. Biochem Biophys Res Commun 293, 463-469 (2002).
18. Pullen, N., et al. Phosphorylation and activation of p70s6k by PDK1. Science 279, 707-710 (1998).
19. Markova, B., et al. Novel pathway in Bcr-Abl signal transduction involves Akt-independent, PLC-gamma1-driven activation of mTOR/p70S6-kinase pathway. Oncogene 29, 739-751 (2010).
20. Grossmann, A., et al. Phospho-tyrosine dependent protein-protein interaction network. Mol Syst Biol 11, 794 (2015).
21. Hossen, M. J., et al. PDK1 disruptors and modulators: a patent review. Expert Opin Ther Pat 25, 513-537 (2015).
22. Hales, E. C., Orr, S. M., Larson Gedman, A., Taub, J. W. & Matherly, L. H. Notch1 receptor regulates AKT protein activation loop (Thr308) dephosphorylation through modulation of the PP2A phosphatase in phosphatase and tensin homolog (PTEN)-null T-cell acute lymphoblastic leukemia cells. J Biol Chem 288, 22836-22848 (2013).
23. Pandey, S. K., Theberge, J. F., Bernier, M. & Srivastava, A. K. Phosphatidylinositol 3-kinase requirement in activation of the ras/C-raf-1/MEK/ERK and p70(s6k) signaling cascade by the insulinomimetic agent vanadyl sulfate. Biochemistry 38, 14667-14675 (1999).
24. Chuu, C. P., et al. Caffeic acid phenethyl ester suppresses the proliferation of human prostate cancer cells through inhibition of p70S6K and Akt signaling networks. Cancer Prev Res (Phila) 5, 788-797 (2012).
25. Junttila, M. R., Li, S. P. & Westermarck, J. Phosphatase-mediated crosstalk between MAPK signaling pathways in the regulation of cell survival. FASEB J 22, 954-965 (2008).

26. Fingar, D. C., Salama, S., Tsou, C., Harlow, E. & Blenis, J. Mammalian cell size is controlled by mTOR and its downstream targets S6K1 and 4EBP1/eIF4E. Genes Dev 16, 1472-1487 (2002).
27. Schalm, S. S. & Blenis, J. Identification of a conserved motif required for mTOR signaling. Curr Biol 12, 632-639 (2002).
28. Oeckinghaus, A., Hayden, M. S. & Ghosh, S. Crosstalk in NF-kappaB signaling pathways. Nat Immunol 12, 695-708 (2011).

In the present specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. The contents of all references, pending patent applications and published patents, cited throughout this application are hereby expressly incorporated by reference as if set forth herein in their entirety, except where terminology is not consistent with the definitions herein. Although specific terms are employed, they are used as in the art unless otherwise indicated.

Table 4: Sources of Related Sequences
Homo sapiens Activated Leukocyte Cell Adhesion Molecule (ALCAM), Transcript Variant 2, mRNA
NCBI Reference Sequence: NM_001243280.1
CD166 Antigen Isoform 2 Precursor [Homo sapiens]
NCBI Reference Sequence: NP_001230209.1.
Mus musculus Activated Leukocyte Cell Adhesion Molecule (Alcam), mRNA
NCBI Reference Sequence: NM_009655.2
CD166 Antigen Precursor [Mus musculus]
NCBI Reference Sequence: NP_033785.1

REFERENCES

1. Vlad, G., R. Cortesini, and N. Suciu-Foca. 2005. License to heal: bidirectional interaction of antigen-specific regulatory T cells and tolerogenic APC. J Immunol 174: 5907-5914.
2. Cella, M., C. Dohring, J. Samaridis, M. Dessing, M. Brockhaus, A. Lanzavecchia, and M. Colonna. 1997. A novel inhibitory receptor (ILT3) expressed on monocytes, macrophages, and dendritic cells involved in antigen processing. J Exp Med 185: 1743-1751.
3. Chang, C. C., R. Ciubotariu, J. S. Manavalan, J. Yuan, A. I. Colovai, F. Piazza, S. Lederman, M. Colonna, R. Cortesini, R. Dalla-Favera, and N. Suciu-Foca. 2002. Tolerization of dendritic cells by T(S) cells: the crucial role of inhibitory receptors ILT3 and ILT4. Nat Immunol 3: 237-243.
4. Manavalan, J. S., P. C. Rossi, G. Vlad, F. Piazza, A. Yarilina, R. Cortesini, D. Mancini, and N. Suciu-Foca. 2003. High expression of ILT3 and ILT4 is a general feature of tolerogenic dendritic cells. Transpl Immunol 11: 245-258.
5. Vlad, G., C. C. Chang, A. I. Colovai, P. Berloco, R. Cortesini, and N. Suciu-Foca. 2009. Immunoglobulin-like transcript 3: A crucial regulator of dendritic cell function. Hum Immunol 70: 340-344.
6. Penna, G., A. Roncari, S. Amuchastegui, K. C. Daniel, E. Berti, M. Colonna, and L. Adorini. 2005. Expression of the inhibitory receptor ILT3 on dendritic cells is dispensable for induction of CD4+Foxp3+ regulatory T cells by 1,25-dihydroxyvitamin D3. Blood 106: 3490-3497.
7. Adorini, L., and G. Penna. 2009. Induction of tolerogenic dendritic cells by vitamin D receptor agonists. Handb Exp Pharmacol: 251-273.
8. Chang, C. C., Z. Liu, G. Vlad, H. Qin, X. Qiao, D. M. Mancini, C. C. Marboe, R. Cortesini, and N. Suciu-Foca. 2009. Ig-like transcript 3 regulates expression of proinflammatory cytokines and migration of activated T cells. J Immunol 182: 5208-5216.
9. Kim-Schulze, S., L. Scotto, G. Vlad, F. Piazza, H. Lin, Z. Liu, R. Cortesini, and N. Suciu-Foca. 2006. Recombinant Ig-like transcript 3-Fc modulates T cell responses via induction of Th anergy and differentiation of CD8+T suppressor cells. J Immunol 176: 2790-2798.
10. Vlad, G., V. D. D'Agati, Q. Y. Zhang, Z. Liu, E. K. Ho, T. Mohanakumar, M. A. Hardy, R. Cortesini, and N. Suciu-Foca. 2008. Immunoglobulin-like transcript 3-Fc suppresses T-cell responses to allogeneic human islet transplants in hu-NOD/SCID mice. Diabetes 57: 1878-1886.
11. Chang, C. C., G. Vlad, V. D. D'Agati, Z. Liu, Q. Y. Zhang, P. Witkowski, A. A. Torkamani, M. B. Stokes, E. K. Ho, R. Cortesini, and N. Suciu-Foca. 2010. BCL6 is required for differentiation of Ig-like transcript 3-Fc-induced CD8+T suppressor cells. J Immunol 185: 5714-5722.
12. van Kempen, L. C., J. M. Nelissen, W. G. Degen, R. Torensma, U. H. Weidle, H. P. Bloemers, C. G. Figdor, and G. W. Swart. 2001. Molecular basis for the homophilic activated leukocyte cell adhesion molecule (ALCAM)-ALCAM interaction. The Journal of biological chemistry 276: 25783-25790.
13. Weidle, U. H., D. Eggle, S. Klostermann, and G. W. Swart. 2010. ALCAM/CD166: cancer-related issues. Cancer Genomics Proteomics 7: 231-243.
14. Swart, G. W. 2002. Activated leukocyte cell adhesion molecule (CD166/ALCAM): developmental and mechanistic aspects of cell clustering and cell migration. Eur J Cell Biol 81: 313-321.
15. Bowen, M. A., D. D. Patel, X. Li, B. Modrell, A. R. Malacko, W. C. Wang, H. Marquardt, M. Neubauer, J. M. Pesando, U. Francke, and et al. 1995. Cloning, mapping, and characterization of activated leukocyte-cell adhesion molecule (ALCAM), a CD6 ligand. J Exp Med 181: 2213-2220.
16. Tanaka, H., T. Matsui, A. Agata, M. Tomura, I. Kubota, K. C. McFarland, B. Kohr, A. Lee, H. S. Phillips, and D. L. Shelton. 1991. Molecular cloning and expression of a novel adhesion molecule, SC1. Neuron 7: 535-545.
17. Burns, F. R., S. von Kannen, L. Guy, J. A. Raper, J. Kamholz, and S. Chang. 1991. DM-GRASP, a novel immunoglobulin superfamily axonal surface protein that supports neurite extension. Neuron 7: 209-220.
18. Bruder, S. P., N. S. Ricalton, R. E. Boynton, T. J. Connolly, N. Jaiswal, J. Zaia, and F. P. Barry. 1998. Mesenchymal stem cell surface antigen SB-10 corresponds to activated leukocyte cell adhesion molecule and is involved in osteogenic differentiation. J Bone Miner Res 13: 655-663.
19. Matsumoto, A., A. Mitchell, H. Kurata, L. Pyle, K. Kondo, H. Itakura, and N. Fidge. 1997. Cloning and characterization of HB2, a candidate high density lipoprotein receptor. Sequence homology with members of the immunoglobulin superfamily of membrane proteins. The Journal of biological chemistry 272: 16778-16782.

20. Kanki, J. P., S. Chang, and J. Y. Kuwada. 1994. The molecular cloning and characterization of potential chick DM-GRASP homologs in zebrafish and mouse. *J Neurobiol* 25: 831-845.
21. Aruffo, A., M. A. Bowen, D. D. Patel, B. F. Haynes, G. C. Starling, J. A. Gebe, and J. Bajorath. 1997. *CD6-ligand interactions: a paradigm for SRCR domain function? Immunol Today* 18: 498-504.
22. Bajorath, J., M. A. Bowen, and A. Aruffo. 1995. Molecular model of the N-terminal receptor-binding domain of the human CD6 ligand ALCAM. *Protein Sci* 4: 1644-1647.
23. Bowen, M. A., J. Bajorath, A. W. Siadak, B. Modrell, A. R. Malacko, H. Marquardt, S. G. Nadler, and A. Aruffo. 1996. The amino-terminal immunoglobulin-like domain of activated leukocyte cell adhesion molecule binds specifically to the membrane-proximal scavenger receptor cysteine-rich domain of CD6 with a 1:1 stoichiometry. *The Journal of biological chemistry* 271: 17390-17396.
24. Gimferrer, I., M. Calvo, M. Mittelbrunn, M. Farnos, M. R. Sarrias, C. Enrich, J. Vives, F. Sanchez-Madrid, and F. Lozano. 2004. Relevance of CD6-mediated interactions in T cell activation and proliferation. *J Immunol* 173: 2262-2270.
25. Hassan, N. J., A. N. Barclay, and M. H. Brown. 2004. Frontline: Optimal T cell activation requires the engagement of CD6 and CD166. *Eur J Immunol* 34: 930-940.
26. Kato, Y., Y. Tanaka, M. Hayashi, K. Okawa, and N. Minato. 2006. Involvement of CD166 in the activation of human gamma delta T cells by tumor cells sensitized with nonpeptide antigens. *J Immunol* 177: 877-884.
27. Patel, D. D., S. F. Wee, L. P. Whichard, M. A. Bowen, J. M. Pesando, A. Aruffo, and B. F. Haynes. 1995. Identification and characterization of a 100-kD ligand for CD6 on human thymic epithelial cells. *J Exp Med* 181: 1563-1568.
28. Singer, N. G., B. C. Richardson, D. Powers, F. Hooper, F. Lialios, J. Endres, C. M. Bott, and D. A. Fox. 1996. Role of the CD6 glycoprotein in antigen-specific and autoreactive responses of cloned human T lymphocytes. *Immunology* 88: 537-543.
29. Singer, N. G., R. Mitra, F. Lialios, B. C. Richardson, R. M. Marks, J. M. Pesando, D. A. Fox, and B. J. Nickoloff. 1997. CD6 dependent interactions of T cells and keratinocytes: functional evidence for a second CD6 ligand on gamma-interferon activated keratinocytes. *Immunol Lett* 58: 9-14.
30. Starling, G. C., G. S. Whitney, A. W. Siadak, M. B. Llewellyn, M. A. Bowen, A. G. Farr, and A. A. Aruffo. 1996. Characterization of mouse CD6 with novel monoclonal antibodies which enhance the allogeneic mixed leukocyte reaction. *Eur J Immunol* 26: 738-746.
31. Zimmerman, A. W., B. Joosten, R. Torensma, J. R. Parnes, F. N. van Leeuwen, and C. G. Figdor. 2006. Long-term engagement of CD6 and ALCAM is essential for T-cell proliferation induced by dendritic cells. *Blood* 107: 3212-3220.
32. Magnoni, C., S. Giudice, G. Pellacani, G. Bertazzoni, C. Longo, E. Veratti, D. Morini, L. Benassi, C. Vaschieri, P. Azzoni, A. De Pol, S. Seidenari, A. Tomasi, A. Pollio, and G. Ponti. 2014. Stem cell properties in cell cultures from different stage of melanoma progression. *Appl Immunohistochem Mol Morphol* 22: 171-181.
33. Hansen, A. G., S. A. Arnold, M. Jiang, T. D. Palmer, T. Ketova, A. Merkel, M. Pickup, S. Samaras, Y. Shyr, H. L. Moses, S. W. Hayward, J. A. Sterling, and A. Zijlstra. 2014. ALCAM/CD166 is a TGF-beta-responsive marker and functional regulator of prostate cancer metastasis to bone. *Cancer Res* 74: 1404-1415.
34. Ihnen, M., E. Kilic, N. Kohler, T. Loning, I. Witzel, C. Hagel, S. Holler, J. F. Kersten, V. Muller, F. Janicke, and K. Milde-Langosch. 2011. Protein expression analysis of ALCAM and CEACAM6 in breast cancer metastases reveals significantly increased ALCAM expression in metastases of the skin. *J Clin Pathol* 64: 146-152.
35. Zhou, J., L. Belov, P. Chapuis, C. Chan, N. Armstrong, K. L. Kaufman, M. J. Solomon, S. J. Clarke, and R. I. Christopherson. 2015. Surface profiles of live colorectal cancer cells and tumor infiltrating lymphocytes from surgical samples correspond to prognostic categories. *J Immunol Methods* 416: 59-68.
36. Fujiwara, K., K. Ohuchida, M. Sada, K. Horioka, C. D. Ulrich, 3rd, K. Shindo, T. Ohtsuka, S. Takahata, K. Mizumoto, Y. Oda, and M. Tanaka. 2014. CD166/ALCAM expression is characteristic of tumorigenicity and invasive and migratory activities of pancreatic cancer cells. *PLoS One* 9: e107247.
37. Ma, L., J. Lin, Y. Qiao, W. Weng, W. Liu, J. Wang, and F. Sun. 2015. Serum CD166: a novel hepatocellular carcinoma tumor marker. *Clin Chim Acta* 441: 156-162.
38. Clauditz, T. S., K. von Rheinbaben, P. Lebok, S. Minner, M. Tachezy, K. Borgmann, R. Knecht, G. Sauter, W. Wilczak, M. Blessmann, and A. Munscher. 2014. Activated leukocyte cell adhesion molecule (ALCAM/CD166) expression in head and neck squamous cell carcinoma (HNSSC). *Pathol Res Pract* 210: 649-655.
39. Porteus, M. H and Baltimore, D. Chimeric nuclease stimulate gene targeting in human cells. Science 300, 763 (2003)
40. Wood, A. J. et al. Targeted genome editing across species using ZFNs and TALENs. Science 333, 307 (2011)
41. Doudna, J. A. and Charpentier, E. The new frontier of genome engineering with CRISPR-Cas9 Science 346, 1077 (2014)
42. Ran F. A. et al. (2013) Genome engineering using the CRISSPR-Cas9 system Nature Protocol 11, 2281 (2013)
43. Cong L et al. (2013) Multiplex genome engineering using CRISPR/Cas systems. Science 339.

What is claimed is:

1. A method comprising administering to a subject having a CD166-expressing cancer a therapeutically effective amount of an agent selected from the group consisting of full length ILT3, the extracellular domain of ILT3 and LT3Fc thereby treating the cancer, wherein the agent inhibits the interaction between ILT3 expressed on monocytes, macrophages, and dendritic cells with CD166 expressed on cancer cells, and the therapeutically effective amount significantly reduces the proliferation of the CD166-expressing cancer cells compared to respective pretreatment levels or significantly increases apoptosis of the CD166-expressing cancer cells compared to a pretreatment level.

2. The method of claim 1, wherein the CD166-expressing cancer is selected from the group consisting of leukemia, lymphoma, prostate, breast, lung, kidney, pancreas, and melanoma cancers.

3. The method of claim 2, wherein the leukemia is chronic myelogenous leukemia (AML), Acute B cell leukemia line or adult T-cell leukemia (T-ALL), and the lymphoma is cutaneous T cell lymphoma.

4. The method of claim 1, wherein the subject is human.

5. The method of claim 1, wherein the agent is administered systemically or locally to the CD166-expressing cancer.

* * * * *

SEQUENCE LISTING

```
<160> NUMBER OF SEQ ID NOS: 10

<210> SEQ ID NO 1
<211> LENGTH: 25
<212> TYPE: DNA
<213> ORGANISM: Artificial Sequence
<220> FEATURE:
<223> OTHER INFORMATION: Synthetic primer: Guide 1 Forward

<400> SEQUENCE: 1
```
caccgaattt ttaggaaaag cccga                                    25

<210> SEQ ID NO 2
<211> LENGTH: 25
<212> TYPE: DNA
<213> ORGANISM: Artificial Sequence
<220> FEATURE:
<223> OTHER INFORMATION: Synthetic primer: Guide 1 Reverse

<400> SEQUENCE: 2
aaactcgggc ttttcctaaa aattc                                    25

<210> SEQ ID NO 3
<211> LENGTH: 25
<212> TYPE: DNA
<213> ORGANISM: Artificial Sequence
<220> FEATURE:
<223> OTHER INFORMATION: Synthetic primer: Guide 2 Forward

<400> SEQUENCE: 3
caccgtgagg cacctacaat agtca                                    25

<210> SEQ ID NO 4
<211> LENGTH: 25
<212> TYPE: DNA
<213> ORGANISM: Artificial Sequence
<220> FEATURE:
<223> OTHER INFORMATION: Synthetic primer: Guide 2 Reverse

<400> SEQUENCE: 4
aaactgacta ttgtaggtgc ctcac                                    25

<210> SEQ ID NO 5
<211> LENGTH: 25
<212> TYPE: DNA
<213> ORGANISM: Artificial Sequence
<220> FEATURE:
<223> OTHER INFORMATION: Synthetic primer: Guide 3 Forward

<400> SEQUENCE: 5
caccgctata gcaggtatct atata                                    25

<210> SEQ ID NO 6
<211> LENGTH: 25
<212> TYPE: DNA
<213> ORGANISM: Artificial Sequence
<220> FEATURE:
<223> OTHER INFORMATION: Synthetic primer: Guide 3 Reverse

<400> SEQUENCE: 6
aaactatata gatacctgct atagc                                    25

<210> SEQ ID NO 7
<211> LENGTH: 25
<212> TYPE: DNA
<213> ORGANISM: Artificial Sequence
<220> FEATURE:
<223> OTHER INFORMATION: Synthetic primer: Guide 4 Forward

<400> SEQUENCE: 7
caccgctctg tagtgtctct atagc                                    25

<210> SEQ ID NO 8
<211> LENGTH: 25
<212> TYPE: DNA

```
<213> ORGANISM: Artificial Sequence
<220> FEATURE:
<223> OTHER INFORMATION: Synthetic primer: Guide 4 Reverse

<400> SEQUENCE: 8
aaacgctata gagacactac agagc                                    25

<210> SEQ ID NO 9
<211> LENGTH: 20
<212> TYPE: DNA
<213> ORGANISM: Artificial Sequence
<220> FEATURE:
<223> OTHER INFORMATION: Synthetic primer: Forward

<400> SEQUENCE: 9
ttgcccaaaa tatccaaacc                                          20

<210> SEQ ID NO 10
<211> LENGTH: 23
<212> TYPE: DNA
<213> ORGANISM: Artificial Sequence
<220> FEATURE:
<223> OTHER INFORMATION: Synthetic primer: Reverse

<400> SEQUENCE: 10
gctcacgaca tttttacatg aca                                      23
```